United States Patent
Hu et al.

(10) Patent No.: US 9,216,186 B2
(45) Date of Patent: Dec. 22, 2015

(54) COMBINATION OF A PYRROLOQUINOLINE COMPOUND AND AN AMINOGLYCODISE ANTIMICROBIAL AGENT

(75) Inventors: Yanmin Hu, London (GB); Anthony R. M. Coates, London (GB)

(73) Assignee: HELPERBY THERAPEUTICS LIMITED, London (GB)

( * ) Notice: Subject to any disclaimer, the term of this patent is extended or adjusted under 35 U.S.C. 154(b) by 0 days.

(21) Appl. No.: 13/814,187

(22) PCT Filed: Aug. 5, 2011

(86) PCT No.: PCT/GB2011/001182
§ 371 (c)(1),
(2), (4) Date: Feb. 14, 2013

(87) PCT Pub. No.: WO2012/017216
PCT Pub. Date: Feb. 9, 2012

(65) Prior Publication Data
US 2013/0137652 A1    May 30, 2013

(30) Foreign Application Priority Data
Aug. 5, 2010  (GB) .................................. 1013207.4

(51) Int. Cl.
*A61K 31/7036* (2006.01)
*A61K 31/4745* (2006.01)
*A61K 31/70* (2006.01)

(52) U.S. Cl.
CPC ......... *A61K 31/7036* (2013.01); *A61K 31/4745* (2013.01); *A61K 31/70* (2013.01)

(58) Field of Classification Search
CPC ........... A61K 31/4745; A61K 2300/00; A61K 36/82; A61K 31/47
USPC ....................................................... 514/40, 41
See application file for complete search history.

(56) References Cited

U.S. PATENT DOCUMENTS
8,207,187 B2 *  6/2012  Beck et al. .................... 514/292

FOREIGN PATENT DOCUMENTS
WO  WO 2007/054693 A1  5/2007
WO  WO 2008/056151 A1 *  5/2008  ......... A61K 31/4439

OTHER PUBLICATIONS
Merck Manual, 1992, 16th Ed., 52-55.*
Hu, Y. et al: "A new approach for the discovery of antibiotics by targeting non-multiplying bacteria: A novel topical antibiotic for *Staphylococcal* infections", PLOS ONE 2010 Public Library of Science USA LNKD-DOI: 10.1371/Journal.Pone.0011818, vol. 5, No. 7, Jul. 2010.

* cited by examiner

*Primary Examiner* — Ganapathy Krishnan
(74) *Attorney, Agent, or Firm* — Steptoe & Johnson LLP

(57) ABSTRACT

This invention relates to the use of 4-methyl-8-phenoxy-1-(2-phenylethyl)-2,3-dihydro-1H-pyrrolo[3,2-c]quinoline or a pharmaceutically acceptable derivative thereof in combination with an aminoglycoside antimicrobial agent for the prevention and/or treatment of microbial infections.

24 Claims, 7 Drawing Sheets

Figure 1 - Kill curve for 4-methyl-8-phenoxy-1-(2-phenylethyl)-2,3-dihydro-1H-pyrrolo[3,2-c]quinoline (4 µg/ml) in combination with kanamycin against *S. aureus*.
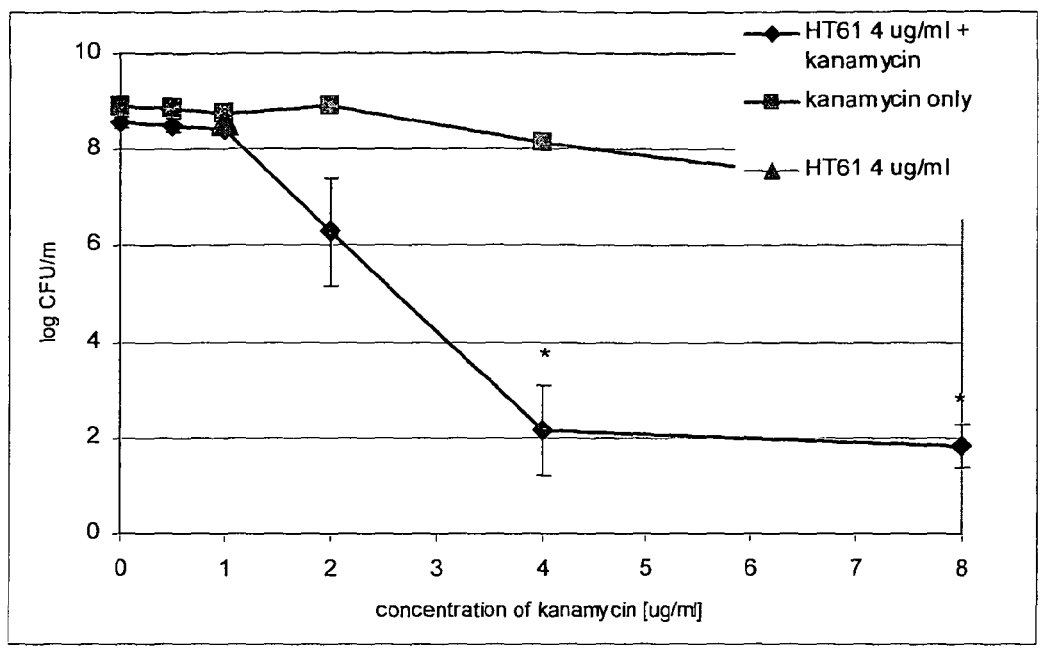
Data are presented as means ± standard deviations, * P < 0.05.

Figure 2 - Kill curve for 4-methyl-8-phenoxy-1-(2-phenylethyl)-2,3-dihydro-1H-pyrrolo[3,2-c]quinoline (4 µg/ml) in combination with gentamicin against *S. aureus*.
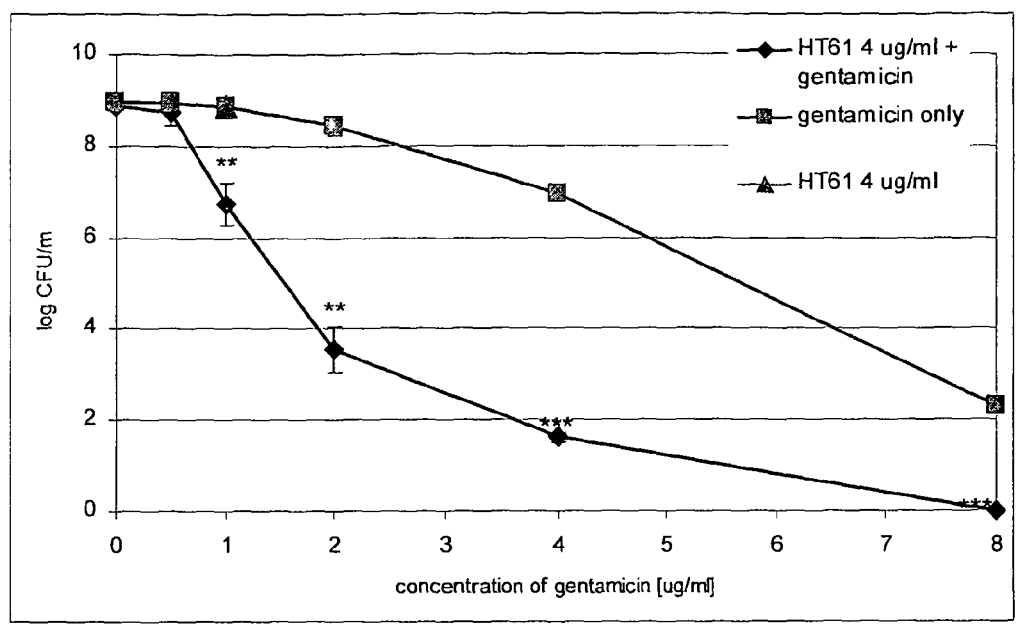
Data are presented as mean ± standard deviations,  $P < 0.001$, * $P < 0.0001$.

Figure 3 - Kill curve for 4-methyl-8-phenoxy-1-(2-phenylethyl)-2,3-dihydro-1H-pyrrolo[3,2-c]quinoline mesylate in combination with tobramycin against *Pseudomonas aeruginosa*
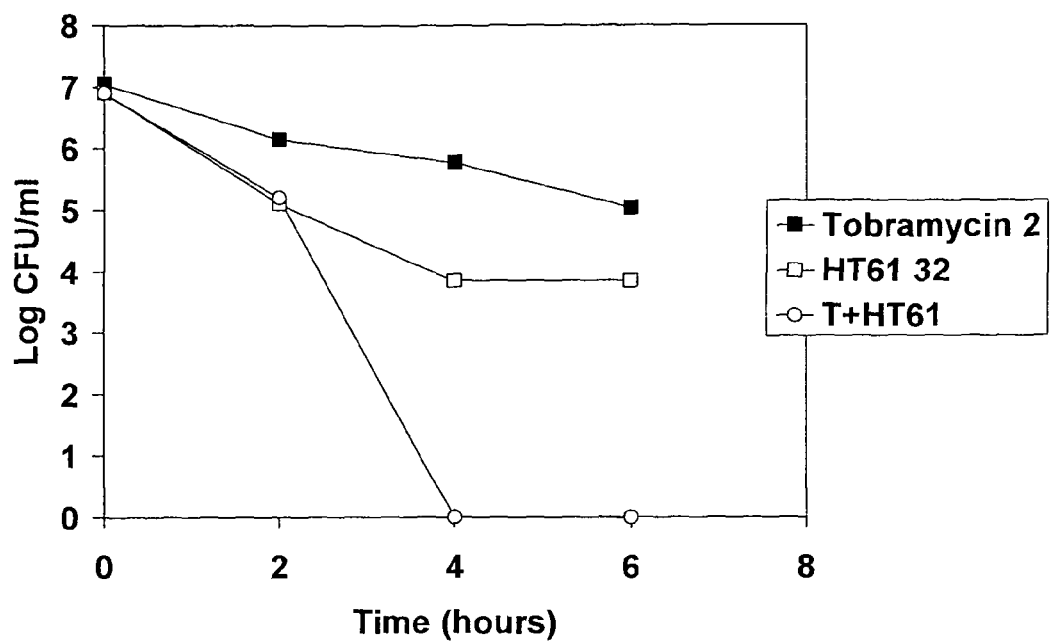

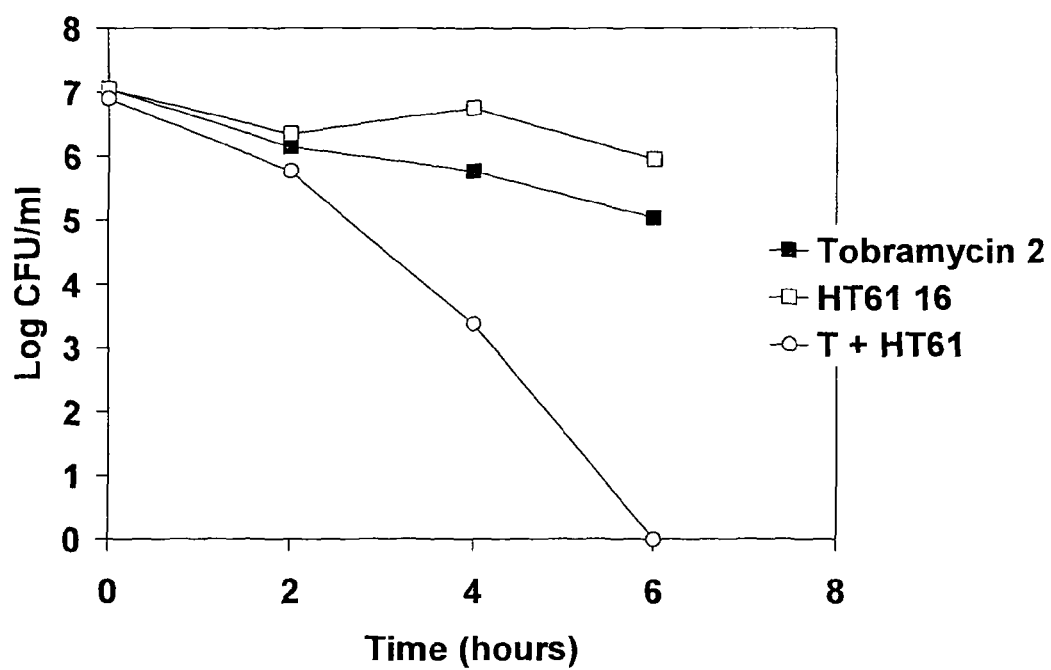
Figure 4 - Kill curve for 4-methyl-8-phenoxy-1-(2-phenylethyl)-2,3-dihydro-1H-pyrrolo[3,2-c]quinoline mesylate in combination with tobramycin against *Pseudomonas aeruginosa*

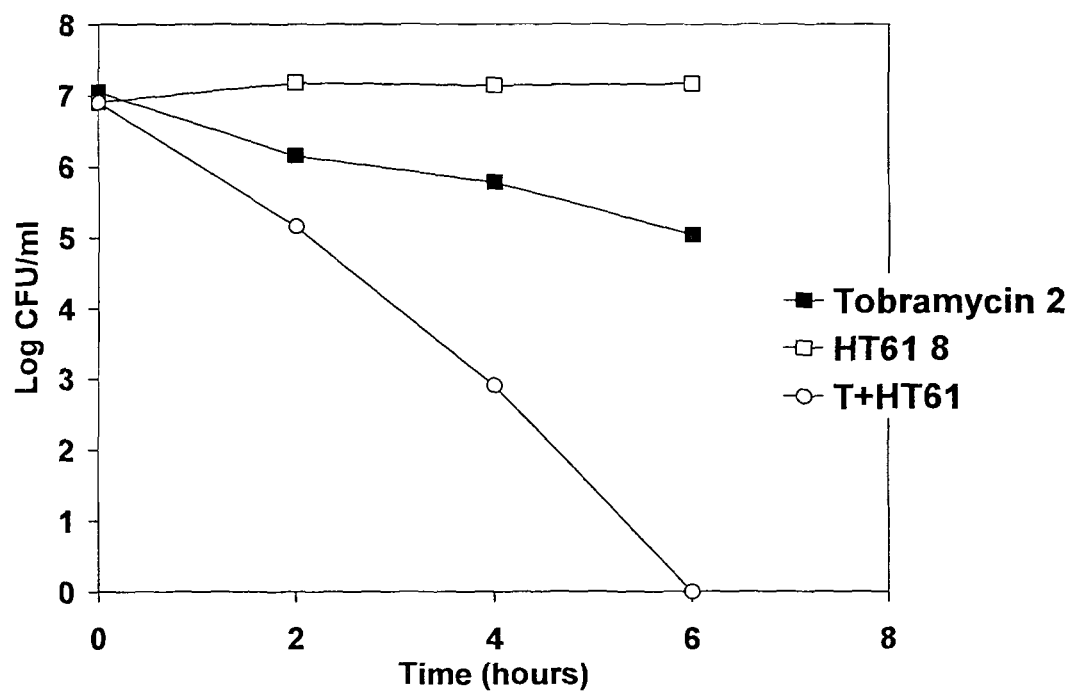
Figure 5 - Kill curve for 4-methyl-8-phenoxy-1-(2-phenylethyl)-2,3-dihydro-1H-pyrrolo[3,2-c]quinoline mesylate in combination with tobramycin against *Pseudomonas aeruginosa*

Figure 6 - Kill curve for 4-methyl-8-phenoxy-1-(2-phenylethyl)-2,3-dihydro-1H-pyrrolo[3,2-c]quinoline mesylate in combination with tobramycin against *Pseudomonas aeruginosa*
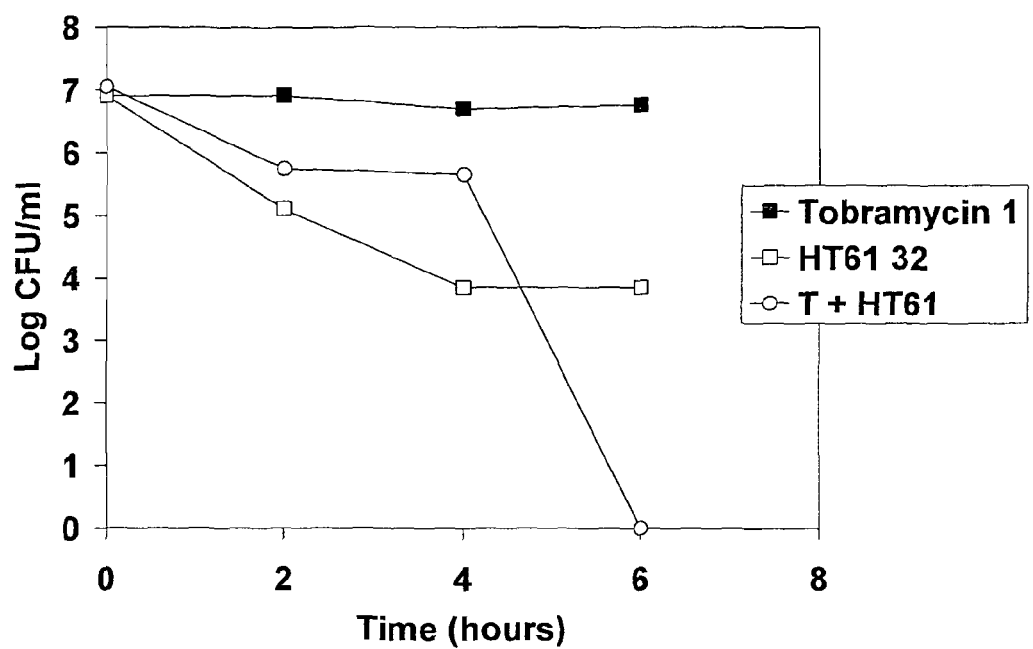

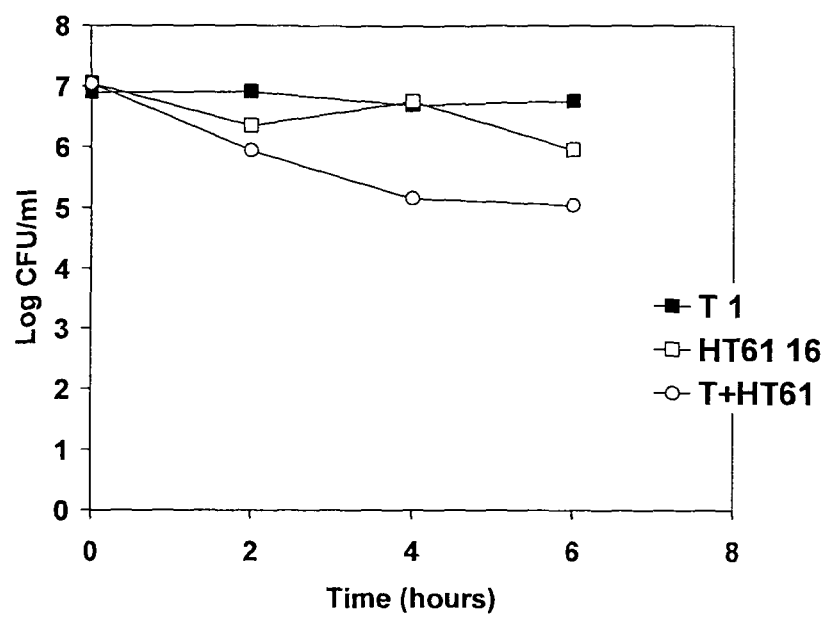
Figure 7 - Kill curve for 4-methyl-8-phenoxy-1-(2-phenylethyl)-2,3-dihydro-1H-pyrrolo[3,2-c]quinoline mesylate in combination with tobramycin against *Pseudomonas aeruginosa*

COMBINATION OF A PYRROLOQUINOLINE COMPOUND AND AN AMINOGLYCODISE ANTIMICROBIAL AGENT

CLAIM FOR PRIORITY

This application claims priority under 35 USC 371 to International Application No. PCT/GB2011/001182, filed on Aug. 5, 2011, which claims priority to British Application No. 1013207.4, filed Aug. 5, 2010, each of which is hereby incorporated by reference in its entirety.

BRIEF DESCRIPTION OF THE DRAWINGS

FIGS. 1 and 2 show the kill curve results for combinations of 4-methyl-8-phenoxy-1-(2-phenylethyl)-2,3-dihydro-1H-pyrrolo[3,2-c]quinoline with kanamycin and gentamicin against *S. aureus*.

FIGS. 3 to 7 show the kill curve results for combinations of 4-methyl-B-phenoxy-1-(2-phenylethyl)-2,3-dihydro-1H-pyrrolo[3,2-c]quinoline mesylate (HT61) with tobramycin (T) against *Pseudomonas aeruginosa*.

DETAILED DESCRIPTION

FIELD OF THE INVENTION

This invention relates to a combination of antimicrobial agents for the prevention and/or treatment of microbial infections. In particular, it relates to the use of 4-methyl-8-phenoxy-1-(2-phenylethyl)-2,3-dihydro-1H-pyrrolo[3,2-c]quinoline or a pharmaceutically acceptable derivative thereof in combination with an aminoglycoside antimicrobial agent.

BACKGROUND

Before the introduction of antibiotics, patients suffering from acute microbial infections (e.g. tuberculosis or pneumonia) had a low chance of survival. For example, mortality from tuberculosis was around 50%. Although the introduction of antimicrobial agents in the 1940s and 1950s rapidly changed this picture, bacteria have responded by progressively gaining resistance to commonly used antibiotics. Now, every country in the world has antibiotic-resistant bacteria. Indeed, more than 70% of bacteria that give rise to hospital acquired infections in the USA resist at least one of the main antimicrobial agents that are typically used to fight infection (*Nature Reviews, Drug Discovery* 1, 895-910 (2002)).

One way of tackling the growing problem of resistant bacteria is the development of new classes of antimicrobial agents. However, until the introduction of linezolid in 2000, there had been no new class of antibiotic marketed for over 37 years. Moreover, even the development of new classes of antibiotic provides only a temporary solution, and indeed there are already reports of resistance of certain bacteria to linezolid (*Lancet* 357, 1179 (2001) and *Lancet* 358, 207-208 (2001)).

In order to develop more long-term solutions to the problem of bacterial resistance, it is clear that alternative approaches are required. One such alternative approach is to minimise, as much as is possible, the opportunities that bacteria are given for developing resistance to important antibiotics. Thus, strategies that can be adopted include limiting the use of antibiotics for the treatment of non-acute infections, as well as controlling which antibiotics are fed to animals in order to promote growth.

However, in order to tackle the problem more effectively, it is necessary to gain an understanding of the actual mechanisms by which bacteria generate resistance to antibiotic agents. To do this requires first a consideration of how current antibiotic agents work to kill bacteria.

Antimicrobial agents target essential components of bacterial metabolism. For example, the β-lactams (e.g. penicillins and cephalosporins) inhibit cell wall synthesis, whereas other agents inhibit a diverse range of targets, such as DNA gyrase (quinolones) and protein synthesis (e.g. macrolides, aminoglycosides, tetracyclines and oxazolidinones). The range of organisms against which the antimicrobial agents are effective varies, depending upon which organisms are heavily reliant upon the metabolic step(s) that is/are inhibited. Further, the effect upon bacteria can vary from a mere inhibition of growth (i.e. a bacteriostatic effect, as seen with agents such as the tetracyclines) to full killing (i.e. a bactericidal effect, as seen, e.g. with penicillin).

Bacteria have been growing on Earth for more than 3 billion years and, in that time, have needed to respond to vast numbers of environmental stresses. It is therefore perhaps not surprising that bacteria have developed a seemingly inexhaustible variety of mechanisms by which they can respond to the metabolic stresses imposed upon them by antibiotic agents. Indeed, mechanisms by which the bacteria can generate resistance include strategies as diverse as inactivation of the drug, modification of the site of action, modification of the permeability of the cell wall, overproduction of the target enzyme and bypass of the inhibited steps. Nevertheless, the rate of resistance emerges to a particular agent has been observed to vary widely, depending upon factors such as the agent's mechanism of action, whether the agent's mode of killing is time- or concentration-dependent, the potency against the population of bacteria and the magnitude and duration of the available serum concentration.

It has been proposed (*Science* 264, 388-393 (1994)) that agents that target single enzymes (e.g. rifampicin) are the most prone to the development of resistance. Further, the longer that suboptimal levels of antimicrobial agent are in contact with the bacteria, the more likely the emergence of resistance.

Moreover, it is now known that many microbial infections include sub-populations of bacteria that are phenotypically resistant to antimicrobials (*J. Antimicrob. Chemother.* 4, 395-404 (1988); *J. Med. Microbiol.* 38, 197-202 (1993); *J. Bacteria* 182, 1794-1801 (2000); ibid. 182, 6358-6365 (2000); ibid. 183, 6746-6751 (2001); *FEMS Microbiol. Lett.* 202, 59-65 (2001); and *Trends in Microbiology* 13, 34-40 (2005)). There appear to be several types of such phenotypically resistant bacteria, including persisters, stationary-phase bacteria, as well as those in the depths of biofilms. However, each of these types is characterised by its low rate of growth compared to log-phase bacteria under the same conditions. Nutritional starvation and high cell densities are also common characteristics of such bacteria.

Although resistant to antimicrobial agents in their slow-growing state, phenotypically resistant bacteria differ from those that are genotypically resistant in that they regain their susceptibility to antimicrobials when they return to a fast-growing state (e.g. when nutrients become more readily available to them).

The presence of phenotypically resistant bacteria in an infection leads to the need for prolonged courses of antimicrobial agents, comprising multiple doses. This is because the resistant, slowly multiplying bacteria provide a pool of "latent" organisms that can convert to a fast-growing state when the conditions allow (thereby effectively re-initiating the infection). Multiple doses over time deal with this issue by gradually killing off the "latent" bacteria that convert to "active" form.

However, dealing with "latent" bacteria by administering prolonged courses of antimicrobials poses its own problems. That is, prolonged exposure of bacteria to suboptimal concentrations of antimicrobial agent can lead to the emergence of genotypically resistant bacteria, which can then multiply rapidly in the presence of even high concentrations of the antimicrobial.

Long courses of antimicrobials are more likely to encourage the emergence of genotypic resistance than shorter courses on the grounds that non-multiplying bacterial will tend to survive and, interestingly, probably have an enhanced ability to mutate to resistance (*Proc. Natl. Acad. Sci. USA* 92, 11736-11740 (1995); *J. Bacteriol.* 179, 6688-6691 (1997); and *Antimicrob. Agents Chemother.* 44, 1771-1777 (2000)).

In the light of the above, a new approach to combating the problem of bacterial resistance might be to select and develop antimicrobial agents on the basis of their ability to kill "latent" microorganisms. The production of such agents would allow, amongst other things, for the shortening of chemotherapy regimes in the treatment of microbial infections, thus reducing the frequency with which genotypical resistance arises in microorganisms.

International Patent Application, Publication Number WO2000028074 describes a method of screening compounds to determine their ability to kill clinically latent microorganisms. Using this method, the Applicant has observed that many conventional antimicrobial agents, such as co-amoxiclav, azithromycin, levofloxacin, linezolid and mupirocin, which otherwise exhibit excellent biological activity against log phase (i.e. multiplying) bacteria, exhibit little or no activity against clinically latent microorganisms. This observation has necessitated the development of novel antimicrobials which may be used to kill clinically latent microorganisms.

International Patent Application, Publication Numbers WO2007054693, WO2008117079 and WO2008142384 describe compounds which exhibit biological activity against clinically latent microorganisms. Examples of such compounds include 4-methyl-8-phenoxy-1-(2-phenylethyl)-2,3-dihydro-1H-pyrrolo[3,2-c]quinoline, 4-(3-benzylpyrrolidin-1-yl)-2-methyl-6-phenoxyquinoline, N-[4-(3-benzylpyrrolidin-1-yl)-2-methylquinolin-6-yl]benzamide and pharmaceutically acceptable derivatives thereof.

A variety of aminoglycoside antimicrobial agents are known. Examples include amikacin, gentamicin, netilmicin, neomycin, streptomycin, tobramycin, amastatin, butirosin, butirosin A, daunorubicin, dibekacin, dihydrostreptomycin, G 418, hygromycin B, kanamycin B, kanamycin, kirromycin, paromomycin, ribostamycin, sisomicin, spectinomycin, streptozocin and thiostrepton.

SUMMARY

The present invention is based upon the unexpected finding that the antimicrobial activity of an aminoglycoside antimicrobial agent is substantially improved if it is administered in combination with the compound 4-methyl-8-phenoxy-1-(2-phenylethyl)-2,3-dihydro-1H-pyrrolo[3,2-c]quinoline. Moreover, this combination of agents has surprisingly been shown to exhibit synergistic antimicrobial activity against certain log phase (i.e. multiplying) and stationary phase (i.e. non-multiplying) microorganisms. The surprising biological activity of the combination of the present invention offers the opportunity to shorten chemotherapy regimes and may result in a reduction in the emergence of microbial resistance associated with the use of such a combination.

Thus, in one embodiment the present invention provides 4-methyl-8-phenoxy-1-(2-phenylethyl)-2,3-dihydro-1H-pyrrolo[3,2-c]quinoline or a pharmaceutically acceptable derivative thereof and an aminoglycoside antimicrobial agent or a pharmaceutically acceptable derivative thereof.

In a further embodiment the present invention provides a combination comprising 4-methyl-8-phenoxy-1-(2-phenylethyl)-2,3-dihydro-1H-pyrrolo[3,2-c]quinoline or a pharmaceutically acceptable derivative thereof and an aminoglycoside antimicrobial agent or a pharmaceutically acceptable derivative thereof.

In another embodiment, the present invention provides the use of 4-methyl-8-phenoxy-1-(2-phenylethyl)-2,3-dihydro-1H-pyrrolo[3,2-c]quinoline or a pharmaceutically acceptable derivative thereof in combination with an aminoglycoside antimicrobial agent or a pharmaceutically acceptable derivative thereof for the manufacture of a medicament for the prevention and/or treatment of a microbial infection; in particular for killing multiplying, non-multiplying and/or clinically latent microorganisms associated with such an infection.

The invention further provides a method of preventing and/or treating a microbial infection, in particular killing multiplying, non-multiplying and/or clinically latent microorganisms associated with such an infection, which comprises administering to a mammal, including man, 4-methyl-8-phenoxy-1-(2-phenylethyl)-2,3-dihydro-1H-pyrrolo[3,2-c]quinoline or a pharmaceutically acceptable derivative thereof in combination with an aminoglycoside antimicrobial agent or a pharmaceutically acceptable derivative thereof.

In another embodiment, the invention provides the use of 4-methyl-8-phenoxy-1-(2-phenylethyl)-2,3-dihydro-1H-pyrrolo[3,2-c]quinoline or a pharmaceutically acceptable derivative thereof in combination with an aminoglycoside antimicrobial agent or a pharmaceutically acceptable derivative thereof for the prevention and/or treatment of a microbial infection; in particular for killing multiplying, non-multiplying and/or clinically latent microorganisms associated with such an infection.

As used herein, the terms "combination" and "in combination with" refer to both separate and sequential administration of 4-methyl-8-phenoxy-1-(2-phenylethyl)-2,3-dihydro-1H-pyrrolo[3,2-c]quinoline or a pharmaceutically acceptable derivative thereof and an aminoglycoside antimicrobial agent or a pharmaceutically acceptable derivative thereof. When the agents are administered sequentially, either 4-methyl-8-phenoxy-1-(2-phenylethyl)-2,3-dihydro-1H-pyrrolo[3,2-c]quinoline or a pharmaceutically acceptable derivative thereof, or an aminoglycoside antimicrobial agent or a pharmaceutically acceptable derivative thereof may be administered first. When administration is simultaneous, the agents may be administered either in the same or a different pharmaceutical composition. Adjunctive therapy, i.e. where one agent is used as a primary treatment and the other agent is used to assist that primary treatment, is also an embodiment of the present invention.

According to a further embodiment of the invention, there is provided a product comprising 4-methyl-8-phenoxy-1-(2-phenylethyl)-2,3-dihydro-1H-pyrrolo[3,2-c]quinoline or a pharmaceutically acceptable derivative thereof and an aminoglycoside antimicrobial agent or a pharmaceutically acceptable derivative thereof as a combined preparation for simultaneous, separate or sequential use in the prevention and/or treatment of a microbial infection, in particular for use in killing multiplying, non-multiplying and/or clinically latent microorganisms associated with a microbial infection.

There is also provided a pharmaceutical composition comprising 4-methyl-8-phenoxy-1-(2-phenylethyl)-2,3-dihydro-1H-pyrrolo[3,2-c]quinoline or a pharmaceutically acceptable derivative thereof, an aminoglycoside antimicrobial agent or a pharmaceutically acceptable derivative thereof and a pharmaceutically acceptable adjuvant, diluent or carrier. Such a composition may be used for the prevention and/or treatment of microbial infections, and in particular for use in killing multiplying, non-multiplying and/or clinically latent microorganisms associated with a microbial infection.

The combination of the present invention may be used to prevent and/or to treat microbial infections. In particular it may be used to kill multiplying, non-multiplying and/or clinically latent microorganisms associated with microbial infections. References herein to the treatment of a microbial infection therefore include killing multiplying, non-multiplying and/or clinically latent microorganisms associated with such infections.

Suitable aminoglycoside antimicrobial agents for use in the combinations of the present invention include one or more agents selected form the group consisting of arbekacin, amikacin, apramycin, gentamicin, netilmicin, neomycin, streptomycin, tobramycin, amastatin, butirosin, butirosin A, daunorubicin, dibekacin, dihydrostreptomycin, G 418, hygromycin B, kanamycin B, kanamycin, kirromycin, paromomycin, rhodostreptomycin, ribostamycin, sisomicin, spectinomycin, streptozocin and thiostrepton, and pharmaceutically acceptable derivatives thereof.

Preferred aminoglycoside antimicrobial agents are kanamycin, gentamicin, tobramycin and neomycin, and pharmaceutically acceptable derivatives thereof. In one embodiment of the invention, the aminoglycoside antimicrobial agent is gentamicin or a pharmaceutically acceptable derivative thereof. In an alternative embodiment of the invention, the aminoglycoside antimicrobial agent is neomycin or a pharmaceutically acceptable derivative thereof. In a further alternative embodiment of the invention, the aminoglycoside antimicrobial agent is kanamycin or a pharmaceutically acceptable derivative thereof. In still a further alternative embodiment of the invention, the aminoglycoside antimicrobial agent is tobramycin or a pharmaceutically acceptable derivative thereof.

As used herein, "kill" means a loss of viability as assessed by a lack of metabolic activity.

As used herein, "clinically latent microorganism" means a microorganism that is metabolically active but has a growth rate that is below the threshold of infectious disease expression. The threshold of infectious disease expression refers to the growth rate threshold below which symptoms of infectious disease in a host are absent.

The metabolic activity of clinically latent microorganisms can be determined by several methods known to those skilled in the art; for example, by measuring mRNA levels in the microorganisms or by determining their rate of uridine uptake. In this respect, clinically latent microorganisms, when compared to microorganisms under logarithmic growth conditions (in vitro or in vivo), possess reduced but still significant levels of:

(I) mRNA (e.g. from 0.0001 to 50%, such as from 1 to 30, 5 to 25 or 10 to 20%, of the level of mRNA); and/or (II) uridine (e.g. [$^3$H]uridine) uptake (e.g. from 0.0005 to 50%, such as from 1 to 40, 15 to 35 or 20 to 30% of the level of [$^3$H]uridine uptake).

Clinically latent microorganisms typically possess a number of identifiable characteristics. For example, they may be viable but non-culturable; i.e. they cannot typically be detected by standard culture techniques, but are detectable and quantifiable by techniques such as broth dilution counting, microscopy, or molecular techniques such as polymerase chain reaction: In addition, clinically latent microorganisms are phenotypically tolerant, and as such are sensitive (in log phase) to the biostatic effects of conventional antimicrobial agents (i.e. microorganisms for which the minimum inhibitory concentration (MIC) of a conventional antimicrobial is substantially unchanged); but possess drastically decreased susceptibility to drug-induced killing (e.g. microorganisms for which, with any given conventional antimicrobial agent, the ratio of minimum microbiocidal concentration (e.g. minimum bactericidal concentration, MBC) to MIC is 10 or more).

As used herein, the term "microorganisms" means fungi and bacteria. References herein to "microbial", "antimicrobial" and "antimicrobially" shall be interpreted accordingly. For example, the term "microbial" means fungal or bacterial, and "microbial infection" means any fungal or bacterial infection.

As used herein, the term "bacteria" (and derivatives thereof, such as "microbial infection") includes, but is not limited to, references to organisms (or infections due to organisms) of the following classes and specific types:

Gram-positive cocci, such as Staphylococci (e.g. *Staph. aureus, Staph. epidermidis, Staph. saprophyticus, Staph. auricularis, Staph. capitis capitis, Staph. c. ureolyticus, Staph. caprae, Staph. cohnii cohnii, Staph. c. urealyticus, Staph. equorum, Staph. gallinarum, Staph. haemolyticus, Staph. hominis hominis, Staph. h. novobiosepticius, Staph. hyicus, Staph. intermedius, Staph. lugdunensis, Staph. pasteuri, Staph. saccharolyticus, Staph. schleiferi schleiferi, Staph. s. coagulans, Staph. sciuri, Staph. simulans, Staph. warneri* and *Staph. xylosus*);

Streptococci (e.g. beta-haemolytic, pyogenic streptococci (such as *Strept. agalactiae, Strept. canis, Strept dysgalactiae dysgalactiae, Strept dysgalactiae equisimilis, Strept equi equi, Strept equi zooepidemicus, Strept. iniae, Strept porcinus* and *Strept. pyogenes*), microaerophilic, pyogenic streptococci (*Streptococcus* "milled", such as *Strept. anginosus, Strept. constellatus constellatus, Strept constellatus pharyngidis* and *Strept intermedius*), oral streptococci of the "mitis" (alpha-haemolytic—*Streptococcus* "viridans", such as *Strept. mitis, Strept. oralis, Strept. sanguinis, Strept. cristatus, Strept gordonii* and *Strept. parasanguinis*), "salivarius" (non-haemolytic, such as *Strept salivarius* and *Strept vestibularis*) and "mutans" (tooth-surface streptococci, such as *Strept. criceti, Strept. mutans, Strept ratti* and *Strept sobrinus*) groups, *Strept. acidominimus, Strept. bovis, Strept. faecalis, Strept. equinus, Strept pneumoniae* and *Strept suis*, or Streptococci alternatively classified as Group A, B, C, D, E, G, L, P, U or V *Streptococcus*);

Gram-negative cocci, such as *Neisseria gonorrhoeae, Neisseria meningitidis, Neisseria cinerea, Neisseria elongata, Neisseria flavescens, Neisseria lactamica, Neisseria mucosa, Neisseria sicca, Neisseria subflava* and *Neisseria weaveri*;

Bacillaceae, such as *Bacillus anthracis, Bacillus subtilis, Bacillus thuringiensis, Bacillus stearothermophilus* and *Bacillus cereus*; Enterobacteriaceae, such as *Escherichia coli, Enterobacter* (e.g. *Enterobacter aerogenes, Enterobacter agglomerans* and *Enterobacter cloacae*), *Citrobacter* (such as *Citrob. freundii* and *Citrob. divernis*), *Hafnia* (e.g. *Hafnia Erwinia* (e.g. *Erwinia persicinus*), *Morganella morganii, Salmonella* (*Salmonella enterica* and *Salmonella typhi*), *Shigella* (e.g. *Shigella dysenteriae, Shigella flexneri,*

Shigella boydii and Shigella sonnei), Klebsiella (e.g. Klebs. pneumoniae, Klebs. oxytoca, Klebs. ornitholytica, Klebs. planticola, Klebs. ozaenae, Klebs. terrigena, Klebs. granulomatis (Calymmatobacterium granulomatis) and Klebs. rhinoscleromatis), Proteus (e.g. Pr. mirabilis, Pr. rettgeri and Pr. vulgaris), Providencia (e.g. Providencia alcalifaciens, Providencia rettgeri and Providencia stuartii), Serratia (e.g. Serratia marcescens and Serratia liquifaciens), and Yersinia (e.g. Yersinia enterocolitica, Yersinia pestis and Yersinia pseudotuberculosis);

Enterococci (e.g. Enterococcus avium, Enterococcus casseliflavus, Enterococcus cecorum, Enterococcus dispar, Enterococcus durans, Enterococcus faecalis, Enterococcus faecium, Enterococcus flavescens, Enterococcus gallinarum, Enterococcus hirae, Enterococcus malodoratus, Enterococcus mundtii, Enterococcus pseudoavium, Enterococcus raffinosus and Enterococcus solitarius); Helicobacter (e.g. Helicobacter pylori, Helicobacter cinaedi and Helicobacter fennelliae);

Acinetobacter (e.g. A. baumanii, A. calcoaceticus, A. haemolyticus, A. johnsonii, A. junii, A. lwoffi and A. radioresistens);

Pseudomonas (e.g. Ps. aeruginosa, Ps. maltophilia (Stenotrophomonas maltophilia), Ps. alcaligenes, Ps. chlororaphis, Ps. fluorescens, Ps. luteola. Ps. mendocina, Ps. monteilii, Ps. oryzihabitans, Ps. pertocinogena, Ps. pseudalcaligenes, Ps. putida and Ps. stutzen); Bacteriodes fragilis;

Peptococcus (e.g. Peptococcus niger);

Peptostreptococcus;

Clostridium (e.g. C. perfringens, C. difficile, C. botulinum, C. tetani, C. absonum, C. argentinense, C. baratii, C. bifermentans, C. beijerinckii, C. butyricum, C. cadaveris, C. camis, C. celatum, C. clostridioforme, C. cochlearium, C. cocleatum, C. fallax, C. ghonii, C. glycolicum, C. haemolyticum, C. hastiforme, C. histolyticum, C. indolis, C. innocuum, C. irregulare, C. leptum, C. limosum, C. malenominatum, C. novyi, C. oroticum, C. paraputrificum, C. piliforme, C. putrefasciens, C. ramosum, C. septicum, C. sordelii, C. sphenoides, C. sporogenes, C. subterminale, C. symbiosum and C. tertium);

Mycoplasma (e.g. M. pneumoniae, M. hominis, M. genitalium and M. urealyticum);

Mycobacteria (e.g. Mycobacterium tuberculosis, Mycobacterium avium, Mycobacterium fortuitum, Mycobacterium marinum, Mycobacterium kansasii, Mycobacterium chelonae, Mycobacterium abscessus, Mycobacterium leprae, Mycobacterium smegmitis, Mycobacterium africanum, Mycobacterium alvei, Mycobacterium asiaticum, Mycobacterium aurum, Mycobacterium bohemicum, Mycobacterium bovis, Mycobacterium branderi, Mycobacterium brumae, Mycobacterium celatum, Mycobacterium chubense, Mycobacterium confluentis, Mycobacterium conspicuum, Mycobacterium cookii, Mycobacterium flavescens, Mycobacterium gadium, Mycobacterium gastri, Mycobacterium genavense, Mycobacterium gordonae, Mycobacterium goodii, Mycobacterium haemophilum, Mycobacterium hassicum, Mycobacterium intracellulare, Mycobacterium interjectum, Mycobacterium heidelberense, Mycobacterium lentiflavum, Mycobacterium malmoense, Mycobacterium microgenicum, Mycobacterium micron, Mycobacterium mucogenicum, Mycobacterium neoaurum, Mycobacterium nonchromogenicum, Mycobacterium peregrinum, Mycobacterium phlei, Mycobacterium scrofulaceum, Mycobacterium shimoidei, Mycobacterium simiae, Mycobacterium szulgai, Mycobacterium terrae, Mycobacterium thermoresistabile, Mycobacterium triplex, Mycobacterium triviale, Mycobacterium tusciae, Mycobacterium ulcerans, Mycobacterium vaccae, Mycobacterium wolinskyi and Mycobacterium xenopi);

Haemophilus (e.g. Haemophilus influenzae, Haemophilus ducreyi, Haemophilus aegyptius, Haemophilus parainfluenzae, Haemophilus haemolyticus and Haemophilus parahaemolyticus);

Actinobacillus (e.g. Actinobacillus actinomycetemcomitans, Actinobacillus equuli, Actinobacillus hominis, Actinobacillus lignieresii, Actinobacillus suis and Actinobacillus ureae);

Actinomyces (e.g. Actinomyces israelii);

Brucella (e.g. Brucella abortus, Brucella canis, Brucella melintensis and Brucella suis);

Campylobacter (e.g. Campylobacter jejuni, Campylobacter coli, Campylobacter lari and Campylobacter fetus);

Listeria monocytogenes;

Vibrio (e.g. Vibrio cholerae and Vibrio parahaemolyticus, Vibrio alginolyticus, Vibrio carchariae, Vibrio fluvialis, Vibrio fumissii, Vibrio hollisae, Vibrio metschnikovii, Vibrio mimicus and Vibrio vulnificus); Erysipelothrix rhusopathiae;

Corynebacteriaceae (e.g. Corynebacterium diphtheriae, Corynebacterium jeikeum and Corynebacterium urealyticum);

Spirochaetaceae, such as Borrelia (e.g. Borrelia recurrentis, Borrelia burgdorferi, Borrelia afzelii, Borrelia andersonfi, Borrelia bissettii, Borrelia garinfi, Borrelia japonica, Borrelia lusitaniae, Borrelia tanukii, Borrelia turdi, Borrelia valaisiana, Borrelia caucasica, Borrelia crocidurae, Borrelia duttoni, Borrelia graingeri, Borrelia hermsii, Borrelia hispanica, Borrelia latyschewii, Borrelia mazzottii, Borrelia parkeri, Borrelia persica, Borrelia turicatae and Borrelia venezuelensis) and Treponema (Treponema pallidum ssp. pallidum, Treponema pallidum ssp. endemicum, Treponema pallidum ssp. pertenue and Treponema carateum);

Pasteurella (e.g. Pasteurella aerogenes, Pasteurella beftyae, Pasteurella canis, Pasteurella dagmatis, Pasteurella gallinarum, Pasteurella haemolytica, Pasteurella multocida multocida, Pasteurella multocida gallicida, Pasteurella multocida septica, Pasteurella pneumotropica and Pasteurella stomatis);

Bordetella (e.g. Bordetella bronchiseptica, Bordetella hinzii, Bordetella holmseii, Bordetella parapertussis, Bordetella pertussis and Bordetella trematum);

Nocardiaceae, such as Nocardia (e.g. Nocardia asteroides and Nocardia brasiliensis);

Rickettsia (e.g. Ricksettsii or Coxiella burnetii);

Legionella (e.g. Legionalla anisa, Legionalla birminghamensis, Legionalla bozemanii, Legionalla cincinnatiensis, Legionalla dumoffii, Legionalla feeleii, Legionalla gormanii, Legionalla hackeliae, Legionalla israelensis, Legionalla jordanis, Legionalla lansingensis, Legionalla longbeachae, Legionalla maceachemii, Legionalla micdadei, Legionalla oakridgensis, Legionalla pneumophila, Legionalla sainthelensi, Legionalla tucsonensis and Legionalla wadsworthii);

Moraxella catarrhalis;

Cyclospora cayetanensis;

Entamoeba histolytica;

Giardia lamblia;

Trichomonas vaginalis;

Toxoplasma gondii;

Stenotrophomonas maltophilia;

Burkholderia cepacia; Burkholderia mallei and Burkholderia pseudomallei;

*Francisella tularensis*;

*Gardnerella* (e.g. *Gardneralla vaginalis* and *Gardneralla mobiluncus*);

*Streptobacillus moniliformis*;

Flavobacteriaceae, such as *Capnocytophaga* (e.g. *Capnocytophaga canimorsus, Capnocytophaga cynodegmi, Capnocytophaga gingivalis, Capnocytophaga granulosa, Capnocytophaga haemolytica, Capnocytophaga ochracea* and *Capnocytophaga sputigena*);

*Bartonella* (*Bartonella bacilliformis, Bartonella clarridgeiae, Bartonella elizabethae, Bartonella henselae, Bartonella quintana* and *Bartonella vinsonii arupensis*);

*Leptospira* (e.g. *Leptospira biflexa, Leptospira borgpetersenii, Leptospira inadai, Leptospira interrogans, Leptospira kirschneri, Leptospira noguchii, Leptospira santarosai* and *Leptospira weilii*);

Spirillium (e.g. *Spirillum minus*);

Baceteroides (e.g. *Bacteroides caccae, Bacteroides capillosus, Bacteroides coagulans, Bacteroides distasonis, Bacteroides eggerthii, Bacteroides forsythus, Bacteroides fragilis, Bacteroides merdae, Bacteroides ovatus, Bacteroides putredinis, Bacteroides pyogenes, Bacteroides splanchinicus, Bacteroides stercoris, Bacteroides tectus, Bacteroides thetaiotaomicron, Bacteroides uniformis, Bacteroides ureolyticus* and *Bacteroides vulgatus*);

*Prevotella* (e.g. *Prevotella bivia, Prevotella buccae, Prevotella corporis, Prevotella dentalis* (*Mitsuokella dentalis*), *Prevotella denticola, Prevotella disiens, Prevotella enoeca, Prevotella heparinolytica, Prevotella intermedia, Prevotella loeschii, Prevotella melaminogenica, Prevotella nigrescens, Prevotella oralis, Prevotella oris, Prevotella oulora, Prevotella tannerae, Prevotella venoralis* and *Prevotella zoogleoformans*);

*Porphyromonas* (e.g. *Porphyromonas asaccharolytica, Porphyromonas cangingivalis, Porphyromonas canoris, Porphyromonas cansulci, Porphyromonas catoniae, Porphyromonas circumdentaria, Porphyromonas crevioricanis, Porphyromonas endodontalis, Porphyromonas gingivalis, Porphyromonas gingivicanis, Porphyromonas levii* and *Porphyromonas macacae*);

*Fusobacterium* (e.g. *F. gonadiaformans, F. mortiferum, F. naviforme, F. necrogenes, F. necrophorum necrophorum, F. necrophorum fundiliforme, F. nucleatum nucleatum, F. nucleatum fusiforme, F. nucleatum polymorphum, F. nucleatum vincentii, F. periodonticum, F. russii, F. ulcerans* and *F. varium*);

*Chlamydia* (e.g. *Chlamydia trachomatis*);

*Cryptosporidium* (e.g. *C. parvum, C. hominis, C. canis, C. fells, C. meleagridis* and *C. muris*);

*Chlamydophila* (e.g. *Chlamydophila abortus* (*Chlamydia psittaci*), *Chlamydophila pneumoniae* (*Chlamydia pneumoniae*) and *Chlamydophila psittaci* (*Chlamydia psittaci*));

*Leuconostoc* (e.g. *Leuconostoc citreum, Leuconostoc cremoris, Leuconostoc dextranicum, Leuconostoc lactis, Leuconostoc mesenteroides* and *Leuconostoc pseudomesenteroides*);

*Gemella* (e.g. *Gemella bergeri, Gemella haemolysans, Gemella morbillorum* and *Gemella sanguinis*); and

*Ureaplasma* (e.g. *Ureaplasma parvum* and *Ureaplasma urealyticum*).

As used herein, the term "fungi" (and derivatives thereof, such as "fungal infection") includes, but is not limited to, references to organisms (or infections due to organisms) of the following classes and specific types:

*Absidia* (e.g. *Absidia corymbifera*);

*Ajellomyces* (e.g. *Ajellomyces capsulatus* and *Ajellomyces dermatitidis*);

*Arthroderma* (e.g. *Arthroderma benhamiae, Arthroderma fulvum, Arthroderma gypseum, Arthroderma incurvatum, Arthroderma otae* and *Arthroderma vanbreuseghemii*);

*Aspergillus* (e.g. *Aspergillus flavus, Aspergillus fumigatus* and *Aspergillus niger*);

*Blastomyces* (e.g. *Blastomyces dermatitidis*);

*Candida* (e.g. *Candida albicans, Candida glabrata, Candida guilliermondii, Candida krusei, Candida parapsilosis, Candida tropicalis* and *Candida pelliculosa*);

*Cladophialophora* (e.g. *Cladophialophora carrionii*);

*Coccidioides* (e.g. *Coccidioides immitis* and *Coccidioides posadasii*);

*Cryptococcus* (e.g. *Cryptococcus neoformans*);

*Cunninghamella* (e.g. *Cunninghamella* sp.)

*Epidermophyton* (e.g. *Epidermophyton floccosum*);

*Exophiala* (e.g. *Exophiala dermatitidis*);

*Filobasidiella* (e.g. *Filobasidiella neoformans*);

*Fonsecaea* (e.g. *Fonsecaea pedrosoi*);

*Fusarium* (e.g. *Fusarium solani*);

*Geotrichum* (e.g. *Geotrichum candidum*);

*Histoplasma* (e.g. *Histoplasma capsulatum*);

*Hortaea* (e.g. *Hortaea werneckii*);

*Issatschenkia* (e.g. *Issatschenkia orientalis*);

*Madurella* (e.g. *Madurella grisae*);

*Malassezia* (e.g. *Malassezia furfur, Malassezia globosa, Malassezia obtusa, Malassezia pachydermatis, Malassezia restricta, Malassezia slooffiae* and *Malassezia sympodialis*);

*Microsporum* (e.g. *Microsporum canis, Microsporum fulvum* and *Microsporum gypseum*);

Microsporidia;

*Mucor* (e.g. *Mucor circinelloides*);

*Nectria* (e.g. *Nectria haematococca*);

*Paecilomyces* (e.g. *Paecilomyces variotii*);

*Paracoccidioides* (e.g. *Paracoccidioides brasiliensis*);

*Penicillium* (e.g. *Penicillium marneffei*);

*Pichia* (e.g. *Pichia anomala* and *Pichia guilliermondii*);

*Pneumocystis* (e.g. *Pneumocystis jiroveci* (*Pneumocystis carinii*));

*Pseudallescheria* (e.g. *Pseudallescheria boydii*);

*Rhizopus* (e.g. *Rhizopus oryzae*);

*Rhodotorula* (e.g. *Rhodotorula rubra*);

*Scedosporium* (e.g. *Scedosporium apiospermum*);

*Schizophyllum* (e.g. *Schizophyllum commune*);

*Sporothrix* (e.g. *Sporothrix schenckii*);

*Trichophyton* (e.g. *Trichophyton mentagrophytes, Trichophyton rubrum, Trichophyton verrucosum* and *Trichophyton violaceum*); and *Trichosporon* (e.g. *Trichosporon asahii, Trichosporon cutaneum, Trichosporon inkin* and *Trichosporon mucoides*).

Particular bacteria that may treated using a combination of the invention include:

Staphylococci, such as *Staph. aureus* (either Methicillin-sensitive (i.e. MSSA) or Methicillin-resistant (i.e. MRSA)) and *Staph. epidermidis*;

Streptococci, such as *Strept. agalactiae* and *Strept. pyogenes*;

Bacillaceae, such as *Bacillus anthracis*;

Enterobacteriaceae, such as *Escherichia coli, Klebsiella* (e.g. *Klebs. pneumoniae* and *Klebs. oxytoca*) and *Proteus* (e.g. *Pr. mirabilis, Pr. rettgeri* and *Pr. vulgaris*);

*Haemophilis influenzae*;

*Pseudomonas* (e.g. *Ps. aeruginosa, Ps. maltophilia* (*Stenotrophomonas maltophilia*), *Ps. alcaligenes, Ps. chlororaphis, Ps. fluorescens, Ps. luteola. Ps. mendocina, Ps. monteilii, Ps. oryzihabitans, Ps. pertocinogena, Ps. pseudalcaligenes, Ps. putida* and *Ps. stutzen*);

Enterococci, such as *Enterococcus faecalis* and *Enterococcus faecium*; and

Mycobacteria, such as *Mycobacterium tuberculosis*.

Preferably, the bacterium is *Staph. aureus*; either MSSA or MRSA.

In an alternative preferred embodiment, the bacterium is *Pseudomonas*, most preferably *Pseudomonas aeruginosa*.

Particular fungi that may be treated with a combination of the invention include *Aspergillus fumigatus, Candida albicans, Cryptococcus neoformans, Histoplasma capsulatum* and *Pneumocystis jiroveci*.

In a preferred embodiment of the invention, there is provided the use of 4-methyl-8-phenoxy-1-(2-phenylethyl)-2,3-dihydro-1H-pyrrolo[3,2-c]quinoline or a pharmaceutically acceptable derivative thereof, preferably the hydrochloride or mesylate salt thereof, in combination with tobramycin or a pharmaceutically acceptable derivative thereof for the prevention and/or treatment of a microbial infection caused by *Pseudomonas aeruginosa*; in particular for killing multiplying, non-multiplying and/or clinically latent microorganisms associated with such an infection.

In a further preferred embodiment of the invention, there is provided the use of 4-methyl-8-phenoxy-1-(2-phenylethyl)-2,3-dihydro-1H-pyrrolo[3,2-c]quinoline or a pharmaceutically acceptable derivative thereof, preferably the hydrochloride or mesylate salt thereof, in combination with kanamycin, gentamicin or a pharmaceutically acceptable derivative thereof for the prevention and/or treatment of a microbial infection caused by *Staphylococcus aureus*, preferably MSSA or MRSA; in particular for killing multiplying, non-multiplying and/or clinically latent microorganisms associated with such an infection.

The combination of the present invention may be used to prevent and/or to treat infections associated with any bacterial or fungal organisms, such as those mentioned above; in particular, it may be used for killing multiplying, non-multiplying and/or clinically latent microorganisms associated with such an infection.

Particular conditions which may be prevented and/or treated using the combination of the present invention include tuberculosis (e.g. pulmonary tuberculosis, non-pulmonary tuberculosis (such as tuberculosis lymph glands, genito-urinary tuberculosis, tuberculosis of bone and joints, tuberculosis meningitis) and miliary tuberculosis), anthrax, abscesses, acne vulgaris, actinomycosis, asthma, bacilliary dysentry, bacterial conjunctivitis, bacterial keratitis, bacterial vaginosis, botulism, Buruli ulcer, bone and joint infections, bronchitis (acute or chronic), brucellosis, burn wounds, cat scratch fever, cellulitis, chancroid, cholangitis, cholecystitis, cutaneous diphtheria, cystic fibrosis, cystitis, diffuse panbronchiolitis, diphtheria, dental caries, diseases of the upper respiratory tract, eczema, empymea, endocarditis, endometritis, enteric fever, enteritis, epididymitis, epiglottitis, erysipelis, erysipelas, erysipeloid, erythrasma, eye infections, furuncles, *gardnerella* vaginitis, gastrointestinal infections (gastroenteritis), genital infections, gingivitis, gonorrhoea, granuloma inguinale, Haverhill fever, infected burns, infections following dental operations, infections in the oral region, infections associated with prostheses, intraabdominal abscesses, Legionnaire's disease, leprosy, leptospirosis, listeriosis, liver abscesses, Lyme disease, lymphogranuloma venerium, mastitis, mastoiditis, meningitis and infections of the nervous system, mycetoma, nocardiosis (e.g. Madura foot), non-specific urethritis, opthalmia (e.g. opthalmia neonatorum), osteomyelitis, otitis (e.g. otitis externa and otitis media), orchitis, pancreatitis, paronychia, pelveoperitonitis, peritonitis, peritonitis with appendicitis, pharyngitis, phlegmons, pinta, plague, pleural effusion, pneumonia, postoperative wound infections, postoperative gas gangrene, prostatitis, pseudo-membranous colitis, psittacosis, pulmonary emphysema, pyelonephritis, pyoderma (e.g. impetigo), Q fever, rat-bite fever, reticulosis, ricin poisoning, Ritter's disease, salmonellosis, salpingitis, septic arthritis, septic infections, septicameia, sinusitis, skin infections (e.g. skin granulomas, impetigo, folliculitis and furunculosis), syphilis, systemic infections, tonsillitis, toxic shock syndrome, trachoma, tularaemia, typhoid, typhus (e.g. epidemic typhus, murine typhus, scrub typhus and spotted fever), urethritis, wound infections, yaws, aspergillosis, candidiasis (e.g. oropharyngeal candidiasis, vaginal candidiasis or balanitis), cryptococcosis, favus, histoplasmosis, intertrigo, mucormycosis, tinea (e.g. tinea corporis, tinea capitis, tinea cruris, tinea pedis and tinea unguium), onychomycosis, pityriasis versicolor, ringworm and sporotrichosis; or infections with MSSA, MRSA, *Staph. epidermidis, Strept. agalactiae, Strept. pyogenes, Escherichia coli, Klebs. pneumoniae, Klebs. oxytoca, Pr. mirabilis, Pr. rettgeri, Pr. vulgaris, Haemophilis influenzae, Enterococcus faecalis* and *Enterococcus faecium*.

References herein to "treatment" extend to prophylaxis as well as the treatment of established diseases or symptoms.

It will be appreciated that one or more additional antimicrobial compounds may also be administered in combination with 4-methyl-8-phenoxy-1-(2-phenylethyl)-2,3-dihydro-1H-pyrrolo[3,2-c]quinoline or a pharmaceutically acceptable derivative thereof and an aminoglycoside antimicrobial agent in accordance with one aspect of the present invention.

Suitable additional antimicrobial compounds for use in the present invention include one or more compounds selected from the following:

(1) β-Lactams, including:
  (i) penicillins, such as
    (I) benzylpenicillin, procaine benzylpenicillin, phenoxy-methylpenicillin, methicillin, propicillin, epicillin, cyclacillin, hetacillin, 6-aminopenicillanic acid, penicillic acid, penicillanic acid sulphone (sulbactam), penicillin G, penicillin V, phenethicillin, phenoxymethylpenicillinic acid, aziocillin, carbenicillin, cloxacillin, D-(−)-penicillamine, dicloxacillin, nafcillin and oxacillin,
    (II) penicillinase-resistant penicillins (e.g. flucloxacillin),
    (III) broad-spectrum penicillins (e.g. ampicillin, amoxicillin, metampicillin and bacampicillin),
    (IV) antipseudomonal penicillins (e.g. carboxypenicillins such as ticarcillin or ureidopenicillins such as piperacillin),
    (V) mecillinams (e.g. pivmecillinam), or
    (VI) combinations of any two or more of the agents mentioned at (I) to (V) above, or combinations of any of the agents mentioned at (I) to (V) above with a δ-lactamase inhibitor such as tazobactam or, particularly, clavulanic acid (which acid is optionally in metal salt form, e.g. in salt form with an alkali metal such as sodium or, particularly, potassium);
  (ii) cephalosporins, such as cefaclor, cefadroxil, cefalexin (cephalexin), cefcapene, cefcapene pivoxil, cefdinir, cefditoren, cefditoren pivoxil, cefixime, cefotaxime, cefpirome, cefpodoxime, cefpodoxime proxetil, cefprozil, cefradine, ceftazidime, cefteram, cefteram pivoxil, ceftriaxone, cefuroxime, cefuroxime axetil, cephaloridine, cephacetrile, cephamandole, cephaloglycine, ceftobiprole, PPI-0903 (TAK-599), 7-aminocephalosporanic acid, 7-aminodes-acetoxycephalosporanic acid, cefamandole, cefazolin, cefmetazole, cefoperazone, cefsulodin, cephalosporin C zinc salt, cephalothin, cephapirin; and (iii) other β-lactams, such as monobactams (e.g. aztreonam), carbapenems (e.g. imipenem (optionally in combination with a renal enzyme inhibitor such as cilastatin), meropenem, ertapenem, doripenem (S-4661) and RO4908463 (CS-023)), penems (e.g. faropenem) and 1-oxa-β-lactams (e.g. moxalactam).

(2) Tetracyclines, such as tetracycline, demeclocycline, doxycycline, lymecycline, minocycline, oxytetracycline, chlortetracycline, meclocycline and methacycline, as well as glycylcyclines (e.g. tigecycline).

(3) One or more additional aminoglycosides, such as amikacin, gentamicin, netilmicin, neomycin, streptomycin, tobramycin, amastatin, butirosin, butirosin A, daunorubicin, dibekacin, dihydrostreptomycin, G 418, hygromycin B, kanamycin B, kanamycin, kirromycin, paromomycin, ribostamycin, sisomicin, spectinomycin, streptozocin and thiostrepton.

(4) (i) Macrolides, such as azithromycin, clarithromycin, erythromycin, roxithromycin, spiramycin, amphotericins B (e.g. amphotericin B), bafilomycins (e.g. bafilomycin A1), brefeldins (e.g. brefeldin A), concanamycins (e.g. concanamycin A), filipin complex, josamycin, mepartricin, midecamycin, nonactin, nystatin, oleandomycin, oligomycins (e.g. oligomycin A, oligomycin B and oligomycin C), pimaricin, rifampicin, rifamycin, rosamicin, tylosin, virginiamycin and fosfomycin.

(ii) Ketolides such as telithromycin and cethromycin (ABT-773).

(iii) Lincosamines, such as lincomycin.

(5) Clindamycin and clindamycin 2-phosphate.

(6) Phenicols, such as chloramphenicol and thiamphenicol.

(7) Steroids, such as fusidic acid (optionally in metal salt form, e.g. in salt form with an alkali metal such as sodium).

(8) Glycopeptides such as vancomycin, teicoplanin, bleomycin, phleomycin, ristomycin, telavancin, dalbavancin and oritavancin.

(9) Oxazolidinones, such as linezolid and AZD2563.

(10) Streptogramins, such as quinupristin and dalfopristin, or a combination thereof.

(11) (i) Peptides, such as polymyxins (e.g. colistin and polymyxin B), lysostaphin, duramycin, actinomycins (e.g. actinomycin C and actinomycin D), actinonin, 7-aminoactinomycin D, antimycin A, antipain, bacitracin, cyclosporin A, echinomycin, gramicidins (e.g. gramicidin A and gramicidin C), myxothiazol, nisin, paracelsin, valinomycin and viomycin.

(ii) Lipopeptides, such as daptomycin.

(iii) Lipoglycopeptides, such as ramoplanin.

(12) Sulfonamides, such as sulfamethoxazole, sulfadiazine, sulfaquinoxaline, sulfathiazole (which latter two agents are optionally in metal salt form, e.g. in salt form with an alkali metal such as sodium), succinylsulfathiazole, sulfadimethoxine, sulfaguanidine, sulfamethazine, sulfamonomethoxine, sulfanilamide and sulfasalazine.

(13) Trimethoprim, optionally in combination with a sulfonamide, such as sulfamethoxazole (e.g. the combination co-trimoxazole).

(14) Antituberculous drugs, such as isoniazid, rifampicin, rifabutin, pyrazinamide, ethambutol, streptomycin, amikacin, capreomycin, kanamycin, quinolones, para-aminosalicylic acid, cycloserine and ethionamide.

(15) Antileprotic drugs, such as dapsone, rifampicin and clofazimine.

(16) (i) Nitroimidazoles, such as metronidazole and timidazole.

(ii) Nitrofurans, such as nitrofurantoin.

(17) Quinolones, such as nalidixic acid, norfloxacin, ciprofloxacin, ofloxacin, levofloxacin, moxifloxacin, gatifloxacin, gemifloxacin, garenoxacin, DX-619, WCK 771 (the arginine salt of S-(−)-nadifloxacin), 8-quinolinol, cinoxacin, enrofloxacin, flumequine, lomefloxacin, oxolinic acid and pipemidic acid.

(18) Amino acid derivatives, such as azaserine, bestatin, D-cycloserine, 1,10-phenanthroline, 6-diazo-5-oxo-L-norleucine and L-alanyl-L-1-aminoethyl-phosphonic acid.

(19) Aureolic acids, such as chromomycin A3, mithramycin A and mitomycin C.

(20) Benzochinoides, such as herbimycin A.

(21) Coumarin-glycosides, such as novobiocin.

(22) Diphenyl ether derivatives, such as irgasan.

(23) Epipolythiodixopiperazines, such as gliotoxin from *Gliocladium fimbriatum*.

(24) Fatty acid derivatives, such as cerulenin.

(25) Glucosamines, such as 1-deoxymannojirimycin, 1-deoxynojirimycin and N-methyl-1-deoxynojirimycin.

(26) Indole derivatives, such as staurosporine.

(27) Diaminopyrimidines, such as iclaprim (AR-100).

(28) Macrolactams, such as ascomycin.

(29) Taxoids, such as paclitaxel.

(30) Statins, such as mevastatin.

(31) Polyphenolic acids, such as (+)-usnic acid.

(32) Polyethers, such as lasalocid A, lonomycin A, monensin, nigericin and salinomycin.

(33) Picolinic acid derivatives, such as fusaric acid.

(34) Peptidyl nucleosides, such as blasticidine S, nikkomycin, nourseothricin and puromycin.

(35) Nucleosides, such as adenine 9-β-D-arabinofuranoside, 5-azacytidine, cordycepin, formycin A, tubercidin and tunicamycin.

(36) Pleuromutilins, such as GSK-565154, GSK-275833 and tiamulin.

(37) Peptide deformylase inhibitors, such as LBM415 (NVP PDF-713) and BB 83698.

(38) Antibacterial agents for the skin, such as fucidin, benzamycin, clindamycin, erythromycin, tetracycline, silver sulfadiazine, chlortetracycline, metronidazole, framycitin, gramicidin, neomycin sulfate, polymyxins (e.g. polymixin B) and gentamycin.

(39) Miscellaneous agents, such as methenamine (hexamine), doxorubicin, piericidin A, stigmatellin, actidione, anisomycin, apramycin, coumermycin A1, L(+)-lactic acid, cytochalasins (e.g. cytochalasin B and cytochalasin D), emetine and ionomycin.

(40) Antiseptic agents, such as chlorhexidine, phenol derivatives (e.g. thymol and triclosan), quarternary ammonium compounds (e.g. benzalkonium chloride, cetylpyridinium chloride, benzethonium chloride, cetrimonium bromide, cetrimonium chloride and cetrimonium stearate), octenidine dihydrochloride, and terpenes (e.g. terpinen-4-ol).

As used herein the term "pharmaceutically acceptable derivative" means:

(a) pharmaceutically acceptable salts; and/or (b) solvates (including hydrates).

Suitable acid addition salts include carboxylate salts (e.g. formate, acetate, trifluoroacetate, propionate, isobutyrate, heptanoate, decanoate, caprate, caprylate, stearate, acrylate, caproate, propiolate, ascorbate, citrate, glucuronate, glutamate, glycolate, α-hydroxybutyrate, lactate, tartrate, phenylacetate, mandelate, phenylpropionate, phenylbutyrate, benzoate, chlorobenzoate, methylbenzoate, hydroxybenzoate, methoxybenzoate, dinitrobenzoate, o-acetoxybenzoate, salicylate, nicotinate, isonicotinate, cinnamate, oxalate, malonate, succinate, suberate, sebacate, fumarate, malate, maleate, hydroxymaleate, hippurate, phthalate or terephthalate salts), halide salts (e.g. chloride, bromide or iodide salts), sulfonate salts (e.g. benzenesulfonate, methyl-, bromo- or chloro-benzenesulfonate, xylenesulfonate, methanesulfonate, ethanesulfonate, propanesulfonate, hydroxyethanesulfonate, 1- or 2-naphthalene-sulfonate or 1,5-naphthalenedisulfonate salts) or sulfate, pyrosulfate, bisulfate, sulfite, bisulfite, phosphate, monohydrogenphosphate, dihydrogenphosphate, metaphosphate, pyrophosphate or nitrate salts, and the like.

A preferred salt form of gentamicin is the sodium salt thereof, gentamicin sodium.

A preferred salt form of kanamycin is the sulphate salt thereof, kanamycin sulphate.

A preferred salt form of tobramycin is the sulphate salt thereof, tobramycin sulphate.

A preferred salt form of neomycin is the sulphate salt thereof, neomycin sulphate.

For the avoidance of doubt, references herein to 4-methyl-8-phenoxy-1-(2-phenylethyl)-2,3-dihydro-1H-pyrrolo[3,2-c]quinoline mean a compound having the following chemical structure:

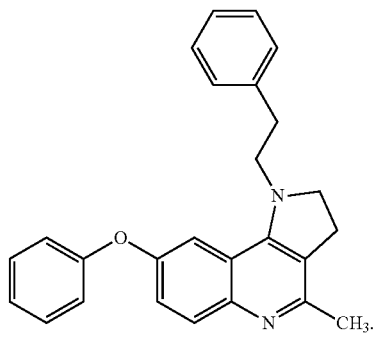 [SMILES: Cc1nc2ccc(Oc3ccccc3)cc2c2c1CCN2CCc1ccccc1]

4-methyl-8-phenoxy-1-(2-phenylethyl)-2,3-dihydro-1H-pyrrolo[3,2-c]quinoline or a pharmaceutically acceptable derivative thereof may be prepared by methods known in the art, for example by following the methods disclosed in International Patent Application, Publication Numbers WO2007054693 and WO2008056151. Preferred pharmaceutically acceptable derivatives of 4-methyl-8-phenoxy-1-(2-phenylethyl)-2,3-dihydro-1H-pyrrolo[3,2-c]quinoline include acid addition salts thereof, particularly the hydrochloride and mesylate salts thereof.

Aminoglycoside antimicrobial agents may be prepared according to known methods and/or are available commercially. For example, tobramycin, kanamycin and gentamicin are commercially available from Sigma Aldrich Ltd.

The compounds of the invention may be administered simultaneously or sequentially and, when administered sequentially, 4-methyl-8-phenoxy-1-(2-phenylethyl)-2,3-dihydro-1H-pyrrolo[3,2-c]quinoline or a pharmaceutically acceptable derivative thereof or an aminoglycoside antimicrobial agent, may be administered first. When administration is simultaneous, the combination may be administered either in the same or a different pharmaceutical composition.

The compounds of the invention may be administered as the raw material but the active ingredients are preferably provided in the form of pharmaceutical compositions.

The active ingredients may be used either as separate formulations or as a single combined formulation. When combined in the same formulation it will be appreciated that the two compounds must be stable and compatible with each other and the other components of the formulation.

Formulations of the invention include those suitable for oral, parenteral (including subcutaneous e.g. by injection or by depot tablet, intradermal, intrathecal, intramuscular e.g. by depot and intravenous), rectal and topical (including dermal, buccal and sublingual) or in a form suitable for administration by inhalation or insufflation administration. The most suitable route of administration may depend upon the condition and disorder of the patient.

Preferably, the compositions of the invention are formulated for oral or topical administration or for administration by inhalation.

The formulations may conveniently be presented in unit dosage form and may be prepared by any of the methods well known in the art of pharmacy e.g. as described in "*Remington: The Science and Practice of Pharmacy*", Lippincott Williams and Wilkins, 21$^{st}$ Edition, (2005). Suitable methods include the step of bringing into association to active ingredients with a carrier which constitutes one or more excipients. In general, formulations are prepared by uniformly and intimately bringing into association the active ingredients with liquid carriers or finely divided solid carriers or both and then, if necessary, shaping the product into the desired formulation. It will be appreciated that when the two active ingredients are administered independently, each may be administered by a different means.

When formulated with excipients, the active ingredients may be present in a concentration from 0.1 to 99.5% (such as from 0.5 to 95%) by weight of the total mixture; conveniently from 30 to 95% for tablets and capsules and 0.01 to 50% for liquid preparations.

A suitable concentration for 4-methyl-8-phenoxy-1-(2-phenylethyl)-2,3-dihydro-1H-pyrrolo[3,2-c]quinoline or a pharmaceutically acceptable derivative thereof is from about 0.1 to about 10%, preferably from about 0.1 to about 5%, for example 0.1, 0.25, 0.5, 1, 2, 3, 4 or 5% by weight of the total mixture.

A suitable concentration for an aminoglycoside antimicrobial agent or a pharmaceutically acceptable derivative thereof is from 0.01 to 10%, for example 0.01, 0.05, 0.1, 0.25, 0.3, 0.5, 1, 2, 3, 4, 5, 6, 7, 8, 9 or 10% by weight of the total mixture.

Formulations suitable for oral administration may be presented as discrete units such as capsules, cachets or tablets (e.g. chewable tablets in particular for paediatric administration), each containing a predetermined amount of active ingredient; as powder or granules; as a solution or suspension in an aqueous liquid or non-aqueous liquid; or as an oil-in-water liquid emulsion or water-in-oil liquid emulsion. The active ingredients may also be presented a bolus, electuary or paste.

A tablet may be made by compression or moulding, optionally with one or more excipients. Compressed tablets may be prepared by compressing in a suitable machine the active ingredient in a free-flowing form such as a powder or granules, optionally mixed with other conventional excipients such as binding agents (e.g. syrup, acacia, gelatin, sorbitol, tragacanth, mucilage of starch, polyvinylpyrrolidone and/or hydroxymethyl cellulose), fillers (e.g. lactose, sugar, microcrystalline cellulose, maize-starch, calcium phosphate and/or sorbitol), lubricants (e.g. magnesium stearate, stearic acid, talc, polyethylene glycol and/or silica), disintegrants (e.g. potato starch, croscarmellose sodium and/or sodium starch glycolate) and wetting agents (e.g. sodium lauryl sulphate). Moulded tablets may be made by moulding in a suitable machine a mixture of the powdered active ingredient with an inert liquid diluent. The tablets may be optionally coated or scored and may be formulated so as to provide controlled release (e.g. delayed, sustained, or pulsed release, or a combination of immediate release and controlled release) of the active ingredients.

Alternatively, the active ingredients may be incorporated into oral liquid preparations such as aqueous or oily suspensions, solutions, emulsions, syrups or elixirs. Formulations containing the active ingredients may also be presented as a dry product for constitution with water or another suitable vehicle before use. Such liquid preparations may contain conventional additives such as suspending agents (e.g. sorbitol syrup, methyl cellulose, glucose/sugar syrup, gelatin, hydroxymethyl cellulose, carboxymethyl cellulose, aluminium stearate gel and/or hydrogenated edible fats), emulsifying agents (e.g. lecithin, sorbitan mono-oleate and/or acacia), non-aqueous vehicles (e.g. edible oils, such as almond oil, fractionated coconut oil, oily esters, propylene glycol and/or ethyl alcohol), and preservatives (e.g. methyl or propyl p-hydroxybenzoates and/or sorbic acid).

Topical compositions, which are useful for treating disorders of the skin or of membranes accessible by digitation (such as membrane of the mouth, vagina, cervix, anus and rectum), include creams, ointments, lotions, sprays, gels and sterile aqueous solutions or suspensions. As such, topical compositions include those in which the active ingredients are dissolved or dispersed in a dermatological vehicle known in the art (e.g. aqueous or non-aqueous gels, ointments, water-in-oil or oil-in-water emulsions). Constituents of such vehicles may comprise water, aqueous buffer solutions, non-aqueous solvents (such as ethanol, isopropanol, benzyl alcohol, 2-(2-ethoxyethoxy)ethanol, propylene glycol, propylene glycol monolaurate, glycofurol or glycerol), oils (e.g. a mineral oil such as a liquid paraffin, natural or synthetic triglycerides such as Miglyol™, or silicone oils such as dimethicone). Depending, inter alia, upon the nature of the formulation as well as its intended use and site of application, the dermatological vehicle employed may contain one or more components selected from the following list: a solubilising agent or solvent (e.g. a β-cyclodextrin, such as hydroxypropyl β-cyclodextrin, or an alcohol or polyol such as ethanol, propylene glycol or glycerol); a thickening agent (e.g. hydroxymethyl cellulose, hydroxypropyl cellulose, carboxymethyl cellulose or carbomer); a gelling agent (e.g. a polyoxyethylene-polyoxypropylene copolymer); a preservative (e.g. benzyl alcohol, benzalkonium chloride, chlorhexidine, chlorbutol, a benzoate, potassium sorbate or EDTA or salt thereof); and pH buffering agent(s) (e.g. a mixture of dihydrogen phosphate and hydrogen phosphate salts, or a mixture of citric acid and a hydrogen phosphate salt). Topical formulations may also be formulated as a transdermal patch.

Methods of producing topical pharmaceutical compositions such as creams, ointments, lotions, sprays and sterile aqueous solutions or suspensions are well known in the art. Suitable methods of preparing topical pharmaceutical compositions are described, e.g. in WO9510999, U.S. Pat. No. 6,974,585, WO2006048747, as well as in documents cited in any of these references.

Topical pharmaceutical compositions according to the present invention may be used to treat a variety of skin or membrane disorders, such as infections of the skin or membranes (e.g. infections of nasal membranes, axilla, groin, perineum, rectum, dermatitic skin, skin ulcers, and sites of insertion of medical equipment such as i.v. needles, catheters and tracheostomy or feeding tubes) with any of the bacteria, fungi described above, (e.g. any of the *Staphylococci, Streptococci, Mycobacteria* or *Pseudomonas* organisms mentioned hereinbefore, such as *S. aureus* (e.g. Methicillin resistant *S. aureus* (MRSA))).

Topical compositions of the invention may be used for pre-operative surgical hand disinfection, antiseptic handwashing, and pre- and post-operative antisepsis for patients undergoing elective surgery.

Particular bacterial conditions that may be treated by topical pharmaceutical compositions of the present invention also include the skin- and membrane-related conditions disclosed hereinbefore, as well as: acne vulgaris; rosacea (including erythematotelangiectatic rosacea, papulopustular rosacea, phymatous rosacea and ocular rosacea); erysipelas; erythrasma; eethyma; eethyma gangrenosum; impetigo; paronychia; cellulitis; folliculitis (including hot tub folliculitis); furunculosis; carbunculosis; staphylococcal scalded skin syndrome; surgical scarlet fever; streptococcal peri-anal disease; streptococcal toxic shock syndrome; pitted keratolysis; trichomycosis axillaris; pyoderma; external canal ear infections; green nail syndrome; spirochetes; necrotizing fasciitis; Mycobacterial skin infections (such as lupus vulgaris, scrofuloderma, warty tuberculosis, tuberculides, erythema nodosum, erythema induratum, cutaneous manifestations of tuberculoid leprosy or lepromatous leprosy, erythema nodosum leprosum, cutaneous *M. kansasii, M. malmoense, M. szulgai, M. simiae, M. gordonae, M. haemophilum, M. avium, M. intracellulare, M. chelonae* (including *M. abscessus*) or *M. fortuitum* infections, swimming pool (or fish tank) granuloma, lymphadenitis and Buruli ulcer (Bairnsdale ulcer, Searles' ulcer, Kakerifu ulcer or Toro ulcer)); as well as infected eczema, burns, abrasions and skin wounds. In a preferred embodiment of the invention, there is provided a topical pharmaceutical composition for the nasal decolonisation of MRSA.

Particular fungal conditions that may be treated by topical pharmaceutical compositions of the present invention also include include the skin- and membrane-related conditions disclosed hereinbefore, as well as: candidiasis; sporotrichosis; ringworm (e.g. tinea pedis, tinea cruris, tinea capitis, tinea unguium or tinea corporis); tinea versicolor; and infections with *Trichophyton, Microsporum, Epidermophyton* or *Pityrosporum ovale* fungi.

Compositions for use according to the invention may be presented in a pack or dispenser device which may contain one or more unit dosage forms containing the active ingredients. The pack may, e.g. comprise metal or plastic foil, such as a blister pack. Where the compositions are intended for administration as two separate compositions these may be presented in the form of a twin pack.

Pharmaceutical compositions may also be prescribed to the patient in "patient packs" containing the whole course of treatment in a single package, usually a blister pack. Patient packs have an advantage over traditional prescriptions, where a pharmacist divides a patients' supply of a pharmaceutical from a bulk supply, in that the patient always has access to the package insert contained in the patient pack, normally missing in traditional prescriptions. The inclusion of the package insert has been shown to improve patient compliance with the physician's instructions.

The administration of the combination of the invention by means of a single patient pack, or patients packs of each composition, including a package insert directing the patient to the correct use of the invention is a further feature of this invention.

According to a further embodiment of the present invention there is provided a patient pack comprising at least one active ingredient of the combination according to the invention, i.e. at least one of 4-methyl-8-phenoxy-1-(2-phenylethyl)-2,3-dihydro-1H-pyrrolo[3,2-c]quinoline or a pharmaceutically acceptable derivative thereof and an aminoglycoside antimicrobial agent, and an information insert containing directions on the use of the combination of the invention.

In another embodiment of the invention, there is provided a double pack comprising in association for separate administration, 4-methyl-8-phenoxy-1-(2-phenylethyl)-2,3-dihydro-1H-pyrrolo[3,2-c]quinoline or a pharmaceutically acceptable derivative thereof and an aminoglycoside antimicrobial agent.

The amount of active ingredients required for use in treatment will vary with the nature of the condition being treated and the age and condition of the patient, and will ultimately be at the discretion of the attendant physician or veterinarian. In general however, doses employed for adult human treatment will typically be in the range of 0.02 to 5000 mg per day, preferably 1 to 1500 mg per day. The desired dose may conveniently be presented in a single dose or as divided doses administered at appropriate intervals, e.g. as two, three, four or more sub-does per day.

Biological Tests

Test procedures that may be employed to determine the biological (e.g. bactericidal or antimicrobial) activity of the active ingredients include those known to persons skilled in the art for determining:

(a) bactericidal activity against clinically latent bacteria; and (b) antimicrobial activity against log phase bacteria.

In relation to (a) above, methods for determining activity against clinically latent bacteria include a determination, under conditions known to those skilled in the art (such as those described in *Nature Reviews, Drug Discovery* 1, 895-910 (2002), the disclosures of which are hereby incorporated by reference), of Minimum Stationary-cidal Concentration ("MSC") or Minimum Dormicidal Concentration ("MDC") for a test compound.

By way of example, WO2000028074 describes a suitable method of screening compounds to determine their ability to kill clinically latent microorganisms. A typical method may include the following steps:

(1) growing a bacterial culture to stationary phase;
(2) treating the stationary phase culture with one or more antimicrobial agents at a concentration and or time sufficient to kill growing bacteria, thereby selecting a phenotypically resistant sub-population;
(3) incubating a sample of the phenotypically resistant subpopulation with one or more test compounds or agents; and
(4) assessing any antimicrobial effects against the phenotypically resistant subpopulation.

According to this method, the phenotypically resistant subpopulation may be seen as representative of clinically latent bacteria which remain metabolically active in vivo and which can result in relapse or onset of disease.

In relation to (b) above, methods for determining activity against log phase bacteria include a determination, under standard conditions (i.e. conditions known to those skilled in the art, such as those described in WO2005014585, the disclosures of which document are hereby incorporated by reference), of Minimum Inhibitory Concentration (MIC) or Minimum Bactericidal Concentration (MBC) for a test compound. Specific examples of such methods are described below.

EXAMPLES

Example 1

In vitro activity of 4-methyl-8-phenoxy-1-(2-phenylethyl)-2,3-dihydro-1H-pyrrolo[3,2-c]quinoline in combination with kanamycin or gentamicin against log phase *S. aureus*

Materials and Methods

Bacterial Strains and Culture Medium

*Staphylococcus aureus* (Oxford); Gram positive; Reference strain.

Nutrient Broth No. 2 (NB) (Oxoid, Cambridge, UK) was used for overnight growth of bacteria.

Iso-Sensitest Broth (Oxoid) was used for evaluation of Minimum inhibitory concentrations (MICs), susceptibility tests for antimicrobials, and efficacy of antimicrobial combinations.

Trypton soya agar (TSA) (Oxoid, Cambridge, UK) was used for growth and quantification of organisms. All media were autoclaved at 121° C. for 15 minutes prior to use.

Bacterial Growth Conditions

Bacterial cultures were prepared by inoculation of 10 ml of NB with a single colony of bacteria on blood agar or TSA and incubated at 37° C. with continuous shaking at 100 rpm for 16 to 24 hours. The overnight cultures were used for experimental tests.

For CFU counting, the bacterial suspensions were diluted using sterile deionized water or phosphate-buffered saline (PBS, Sigma Aldrich Ltd, Poole, Dorset, UK). 100 µl of 10-fold serial dilutions of bacteria culture were plated on one third of TSA plates in triplicate and incubated 24 to 48 hours at 37° C. The number of cells presented on the plates was counted using an AcoLyte colony counter (Synbiosis) and results were expressed as Colony Forming Units/ml (CFU/ml).

Antibiotics

Kanamycin and gentamicin were purchased from Sigma Aldrich Ltd.

4-methyl-8-phenoxy-1-(2-phenylethyl)-2,3-dihydro-1H-pyrrolo[3,2-c]quinoline (in hydrochloride salt form) was provided by Helperby Therapeutics.

Stocks of 10 mg/ml of kanamycin, gentamicin and 4-methyl-8-phenoxy-1-(2-phenylethyl)-2,3-dihydro-1H-pyrrolo[3,2-c]quinoline were prepared by dilution in dimethyl sulfoxide (DMSO) or water respectively. The antibiotic solutions were stored at −20° C.

Evaluation of MIC and MBC

Minimum inhibitory concentration (MIC) analyses for kanamycin, gentamicin and 4-methyl-8-phenoxy-1-(2-phenylethyl)-2,3-dihydro-1H-pyrrolo[3,2-c]quinoline were performed in Iso-Sensitest broth using a broth dilution method and were determined as the lowest concentration of antimicrobial agent that inhibited visible growth after overnight incubation at 37° C. The stock solution of each drug was diluted to required concentrations. 10 µl of drug from each dilution was taken and mixed with 290 µl of culture with $10^6$ of bacterial cells on a 96-well plate to make the final required concentrations (µg/ml).

The plates were read at 405 nm using a 96-well plate reader Elx 800 equipped with a 405-nm filter (Bio-Tek) before and after incubation. The MIC values of the drugs were determined by comparison of the optical density reading between prior and post drug treatment.

Minimum bactericidal concentration (MBC) was determined by subculturing 100 μl of dilutions from the 96-well plate on fresh drug-free TSA agar plates and incubating further for 24 to 48 hours at 37° C. The highest dilution that showed no single bacterial colony on TSA plates was taken as the MBC.

Efficacy of Antimicrobial Combinations

The antimicrobial activity of 4-methyl-8-phenoxy-1-(2-phenylethyl)-2,3-dihydro-1H-pyrrolo[3,2-c]quinoline in combination with (a) kanamycin and (b) gentamicin against *S. aureus*, in a concentration range from below to above the MIC, was assessed in a suspension assay by the time-kill curve method.

Serial double dilutions of the antimicrobial compounds were prepared as follows: 4-methyl-8-phenoxy-1-(2-phenylethyl)-2,3-dihydro-1H-pyrrolo[3,2-c]quinoline from 16 μg/ml to 0.25 μg/ml; kanamycin from 4 to 0.24 μg/ml; and gentamicin from 8 to 0.5 μg/ml. Ten microliters of each antimicrobial solution were added to the rows of a 96-well microtitre plate in diminishing concentrations, and then 10 μl of 4-methyl-8-phenoxy-1-(2-phenylethyl)-2,3-dihydro-1H-pyrrolo[3,2-c]quinoline was added to the columns in decreasing concentrations. The wells were then inoculated with 280 μl of *S. aureus* (Oxford strain) suspension containing $10^7$ CFU/ml of inocula. Drug free controls were also included.

The microtitre plates were incubated at 37° C. for 16 to 24 hours, read in a 96-well plate reader, then samples were diluted and 100 μl of each dilution was plated out on TSA plates. After 24 to 48 hours incubation CFU was counted. Each test was performed in triplicate and repeated twice. Synergy was defined as a 2 $\log_{10}$ decrease in colony counts, when antibacterial activity of combinations was compared with that of the most active single agent.

Statistical Analysis

The mean bacterial colony count at varying time points was compared by the two-tailed t-test with unequal variance. P values of ≤1.05 indicated significant difference.

Results

Determination of susceptibility of *S. Aureus* to kanamycin, qentamicin and 4-methyl-8-phenoxy-1-(2-phenylethyl)-2,3-dihydro-1H-pyrrolo[3,2-c]quinoline

| Antimicrobial agent | MIC (μg/ml) | MBC (μg/ml) |
|---|---|---|
| Kanamycin | 8 | — |
| Gentamicin | 1 | 8 |
| 4-methyl-8-phenoxy-1-(2-phenylethyl)-2,3-dihydro-1H-pyrrolo[3,2-c]quinoline | 8 | 16 |

Time-kill studies for 4-methyl-8-phenoxy-1-(2-phenylethyl)-2,3-dihydro-1H-pyrrolo[3,2-c]quinoline in combination with (a) kanamycin and (b) gentamicin The kill curve results for combinations of 4-methyl-8-phenoxy-1-(2-phenylethyl)-2,3-dihydro-1H-pyrrolo[3,2-c]quinoline (4 μg/ml) with kanamycin and gentamicin against *S. aureus* are shown in FIGS. 1 and 2. Results are displayed as means of log reduction in viable organisms±standard deviation (*P<0.005, P<0.001 and *P<0.0001).

The growth control for these experiments is not shown but was grossly turbid during the time of experiments.

Conclusions

Significant synergistic activities were observed for kanamycin (2, 4 and 8 μg/ml) in combination with 4-methyl-8-phenoxy-1-(2-phenylethyl)-2,3-dihydro-1H-pyrrolo[3,2-c]quinoline (4 μg/ml).

Similar synergies were observed for gentamicin (8, 4, 2 and 1 μg/ml) in combination with 4-methyl-8-phenoxy-1-(2-phenylethyl)-2,3-dihydro-1H-pyrrolo[3,2-c]quinoline (4 μg/ml).

Example 2

In vitro activity of 4-methyl-8-phenoxy-1-(2-phenylethyl)-2,3-dihydro-1H-pyrrolo[3,2-c]quinoline in combination with tobramycin against stationary phase *Pseudomonas aeruginosa*

Materials and Methods
Bacterial Strains and Culture Medium

*Pseudomonas aeruginosa* (clinical isolate).

Bacterial Growth Conditions

A single colony of *Ps. aeruginosa* was inoculated in 10 ml of Nutrient Broth No. 2 (NB) (Oxoid) which was incubated overnight at 37° C. with continuous shaking at 120 rpm. 200 μl of the overnight culture was added into a 500 ml screw-cap which contained 100 ml of NB. The 100 ml culture was incubated at 37° C. with continuous shaking for 5 to 6 days. The cultures were diluted with phosphate buffered saline to $10^7$ CFU/ml.

Antibiotics

Tobramycin was purchased from Sigma Aldrich Ltd.

4-methyl-8-phenoxy-1-(2-phenylethyl)-2,3-dihydro-1H-pyrrolo[3,2-c]quinoline (in mesylate salt form) was provided by Helperby Therapeutics.

Stocks of 10 mg/ml of tobramycin and 4-methyl-8-phenoxy-1-(2-phenylethyl)-2,3-dihydro-1H-pyrrolo[3,2-c]quinoline mesylate were prepared by dilution in water. The antibiotic solutions were stored at −20° C.

The bacterial cell suspension was incubated with tobramycin and 4-methyl-8-phenoxy-1-(2-phenylethyl)-2,3-dihydro-1H-pyrrolo[3,2-c]quinoline mesylate at different concentrations. The activities of the combination and each of the individual drugs were measured by CFU counts at 0, 2, 4, 6 and 8 hours. CFU counts were performed as follows: from serial 10-fold dilutions of the experimental cultures, 100 μl samples were added to triplicate plates of nutrient agar plates (Oxoid). Colony forming units (CFU) were counted after incubation of the plates at 37° C. for 24 hours.

Results

The kill curve results for combinations of 4-methyl-8-phenoxy-1-(2-phenylethyl)-2,3-dihydro-1H-pyrrolo[3,2-c]quinoline mesylate (HT61) (32, 16 or 8 μg/ml) with tobramycin (T) (2 or 1 μg/ml) against *Pseudomonas aeruginosa* are shown in FIGS. 3 to 7. Results are displayed as means of log reduction in viable organisms±standard deviation (*P<0.005, P<0.001 and *P<0.0001).

Conclusions 4-methyl-8-phenoxy-1-(2-phenylethyl)-2,3-dihydro-1H-pyrrolo[3,2-c]quinoline mesylate alone at 32, 16 and 8 μg/ml showed slight or no activities against stationary phase *P. aeruginosa*. In addition, tobramycin alone at 2 and 1 μg/ml had very low or no activities. However, tobramycin in combination with 4-methyl-8-phenoxy-1-(2-phenylethyl)-2,3-dihydro-1H-pyrrolo[3,2-c]quinoline mesylate killed the bacteria rapidly. The CFU counts reached 0 at 4 or 6 hours after incubation. These data are indicative of synergistic activity.

Example 3

In vitro activity of 4-methyl-8-phenoxy-1-(2-phenylethyl)-2,3-dihydro-1H-pyrrolo[3,2-c]quinoline in combination with tobramycin against log phase Pseudomonas aeruginosa by chequerboard analysis Materials and Methods
Bacterial Strains and Culture Medium
  Pseudomonas aeruginosa (clinical isolate).
  Nutrient Broth No. 2 (NB) (Oxoid, Cambridge, UK) was used for overnight growth of bacteria.
  Iso-Sensitest Broth (Oxoid) was used for evaluation of Minimum inhibitory concentrations (MICs).
Bacterial Growth Conditions
  P. aeruginosa was grown in 10 ml of NB overnight at 37° C. with continuous shaking at 120 rpm. The overnight cultures were diluted 1000× with iso-sensitest broth to obtain a cell suspension containing the bacteria at $10^6$ CFU/ml. The cultures were incubated at 37° C. with shaking for 1-2 hours served as log-phase cultures. Viability of the bacteria was estimated by colony forming unit (CFU) counts.
Antibiotics
  Tobramycin was purchased from Sigma Aldrich Ltd.
  4-methyl-8-phenoxy-1-(2-phenylethyl)-2,3-dihydro-1H-pyrrolo[3,2-c]quinoline (in mesylate salt form) was provided by Helperby Therapeutics.
Drug Assay of Log Phase Bacteria
  The combinations of tobramycin and 4-methyl-8-phenoxy-1-(2-phenylethyl)-2,3-dihydro-1H-pyrrolo[3,2-c] quinoline mesylate were prepared using 96 well plates using the drug concentrations starting from 16 µg/ml for tobramycin and 64 ug/ml for HT61. The two drugs were serially diluted twofold to 0 and combined in a pattern of an array.

Compound Preparation
  Stocks of 10 mg/ml of tobramycin and 4-methyl-8-phenoxy-1-(2-phenylethyl)-2,3-dihydro-1H-pyrrolo[3,2-c] quinoline mesylate were prepared by dilution in water. The antibiotic solutions were stored at −20° C.
Determination of Activities
  The optical density of the bacterial cells was read at 405 nm using a plate reader (Bio TEK). The MIC concentration was determined as the lowest concentration of drug which inhibits the bacterial growth. The MIC values of the drugs were determined by comparison of the optical density reading between prior and post drug treatment.
Results

|  |  | Tobramycin | | | | | | | | | | |
|---|---|---|---|---|---|---|---|---|---|---|---|---|
| | µg/ml | 16 | 8 | 4 | 2 | 1 | 0.5 | 0.25 | 0.125 | 0.0625 | 0.03125 | 0.01563 | 0 |
| HT61 | 64 | 0.53 | 0.85 | 0.85 | 0.82 | 1.02 | 0.84 | 2.73 | 2.85 | 2.88 | 2.92 | 2.99 | 3.01 |
| | 32 | 0.42 | 0.52 | 0.52 | 0.51 | 0.52 | 0.61 | 3.00 | 3.04 | 3.13 | 3.13 | 3.13 | 3.09 |
| | 16 | 0.27 | 0.45 | 0.44 | 0.44 | 0.45 | 1.45 | 3.04 | 3.15 | 3.08 | 3.10 | 3.23 | 3.11 |
| | 8 | 0.24 | 0.44 | 0.43 | 0.43 | 0.44 | 2.24 | 3.06 | 3.10 | 3.13 | 3.14 | 3.16 | 3.15 |
| | 4 | 0.24 | 0.44 | 0.44 | 0.43 | 1.12 | 2.19 | 2.98 | 3.09 | 3.09 | 3.12 | 3.13 | 3.11 |
| | 2 | 0.24 | 0.43 | 0.44 | 0.44 | 0.44 | 2.00 | 3.07 | 3.18 | 3.14 | 3.11 | 3.23 | 3.12 |
| | 1 | 0.24 | 0.44 | 0.43 | 0.44 | 0.44 | 1.97 | 3.07 | 3.11 | 3.15 | 3.16 | 3.17 | 3.16 |
| | 0 | 0.23 | 0.44 | 0.47 | 0.44 | 0.46 | 2.19 | 3.04 | 3.15 | 3.16 | 3.24 | 3.25 | 3.25 |

|  |  | Tobramycin | | | | | | | | | | |
|---|---|---|---|---|---|---|---|---|---|---|---|---|
| | | 16 | 8 | 4 | 2 | 1 | 0.5 | 0.25 | 0.125 | 0.0625 | 0.03125 | 0.01563 | 0 |
| HT61 | 64 | 0.83 | 0.78 | 0.79 | 0.81 | 0.81 | 0.83 | 2.71 | 2.86 | 2.89 | 2.91 | 2.94 | 3.09 |
| | 32 | 0.54 | 0.50 | 0.52 | 0.53 | 0.53 | 0.65 | 2.95 | 2.99 | 3.05 | 3.11 | 3.10 | 3.04 |
| | 16 | 0.48 | 0.44 | 0.44 | 0.44 | 0.45 | 0.83 | 3.01 | 3.18 | 3.05 | 3.06 | 3.24 | 3.07 |
| | 8 | 0.43 | 0.44 | 0.43 | 0.44 | 0.43 | 2.26 | 3.06 | 3.06 | 3.07 | 3.11 | 3.14 | 3.10 |
| | 4 | 0.49 | 0.44 | 0.46 | 0.44 | 0.45 | 2.40 | 3.01 | 3.06 | 3.07 | 3.10 | 3.15 | 3.10 |
| | 2 | 0.44 | 0.44 | 0.44 | 0.44 | 0.44 | 1.97 | 2.95 | 3.07 | 3.09 | 3.16 | 3.14 | 3.11 |
| | 1 | 0.43 | 0.44 | 0.44 | 0.43 | 0.44 | 1.98 | 3.01 | 3.02 | 3.08 | 3.12 | 3.13 | 3.08 |
| | 0 | 0.48 | 0.44 | 0.50 | 0.45 | 0.46 | 2.18 | 2.97 | 3.08 | 3.09 | 3.18 | 3.14 | 3.28 |

4-methyl-8-phenoxy-1-(2-phenylethyl)-2,3-dihydro-1H-pyrrolo[3,2-c]quinoline mesylate alone has no MIC against P. aeruginosa. Tobramycin MIC was 1 µg/ml. However, with tobramycin at 0.5 µg/ml, HT61 MIC was observed at 16 µg/ml.

Conclusions
  There was no MIC shown for 4-methyl-8-phenoxy-1-(2-phenylethyl)-2,3-dihydro-1H-pyrrolo[3,2-c]quinoline mesylate within the concentration range used. Tobramycin MIC was 1 µg/ml. However, in combination with tobramycin 0.5 µg/ml, an MIC of 4-methyl-8-phenoxy-1-(2-phenylethyl)-2,3-dihydro-1H-pyrrolo[3,2-c]quinoline mesylate was observed at 16 µg/ml. There was a combined activity seen when 4-methyl-8-phenoxy-1-(2-phenylethyl)-2,3-dihydro-1H-pyrrolo[3,2-c]quinoline mesylate was used in combination with tobramycin.

The invention claimed is:

1. A combination comprising 4-methyl-8-phenoxy-1-(2-phenylethyl)-2,3-dihydro-1H-pyrrolo[3,2-c]quinoline, or a salt thereof, and an aminoglycoside antimicrobial agent.

2. A combination according to claim 1 comprising 4-methyl-8-phenoxy-1-(2-phenylethyl)-2,3-dihydro-1H-pyrrolo[3,2-c]quinoline hydrochloride.

3. A combination according to claim 1 comprising 4-methyl-8-phenoxy-1-(2-phenylethyl)-2,3-dihydro-1H-pyrrolo[3,2-c]quinoline mesylate.

4. A combination according to claim 1 wherein the aminoglycoside antimicrobial agent is selected from the group consisting of arbekacin, amikacin, apramycin, gentamicin, netilmicin, neomycin, streptomycin, tobramycin, amastatin, butirosin, butirosin A, daunorubicin, dibekacin, dihydrostreptomycin, Geneticin (G 418), hygromycin B, kanamycin B, kanamycin, kirromycin, paromomycin, rhodostreptomycin, ribostamycin, sisomicin, spectinomycin, streptozocin and thiostrepton.

5. A combination according to claim 4 wherein the aminoglycoside antimicrobial agent is neomycin, kanamycin, gentamicin or tobramycin.

6. A method of manufacture of a medicament comprising combining 4-methyl-8-phenoxy-1-(2-phenylethyl)-2,3-dihydro-1H-pyrrolo[3,2-c]quinoline, or a pharmaceutically salt or solvate thereof, with an aminoglycoside antimicrobial agent, or a pharmaceutically acceptable salt or solvate thereof.

7. A method of treatment of a microbial infection comprising simultaneously, separately or sequentially administering a combination comprising 4-methyl-8-phenoxy-1-(2-phenylethyl)-2,3-dihydro-1H-pyrrolo[3,2-c]quinoline and an aminoglycoside antimicrobial agent to a patient in need thereof.

8. The method according to claim 7 wherein the infection is a bacterial infection.

9. The method according to claim 8 wherein the infection is caused by *Staphylococci, Streptococci, Pseudomonas, Bacillaceae, Enterobacteriaceae, Haemophilis influenzae, Enterococci, Mycobacteria*.

10. The method according to claim 9 wherein the infection is caused by *Staphylococcus aureus*.

11. The method according to claim 9 wherein the infection is caused by *Pseudomonas aeruginosa*.

12. The method according to claim 7 wherein the microbial infection is a fungal infection.

13. The method according to claim 12 wherein the infection is caused by *Aspergillus fumigatus, Candida albicans, Cryptococcus neoformans, Histoplasma capsulatum* and *Pneumocystis jiroveci*.

14. The method according to claim 7 for the treatment of tuberculosis, anthrax, abscesses, acne vulgaris, actinomycosis, asthma, bacilliary dysentry, bacterial conjunctivitis, bacterial keratitis, bacterial vaginosis, botulism, Buruli ulcer, bone and joint infections, bronchitis (acute or chronic), brucellosis, burn wounds, cat scratch fever, cellulitis, chancroid, cholangitis, cholecystitis, cutaneous diphtheria, cystic fibrosis, cystitis, diffuse panbronchiolitis, diphtheria, dental caries, diseases of the upper respiratory tract, eczema, empymea, endocarditis, endometritis, enteric fever, enteritis, epididymitis, epiglottitis, erysipelis, erysipclas, erysipeloid, erythrasma, eye infections, furuncles, gardnerella vaginitis, gastrointestinal infections (gastroenteritis), genital infections, gingivitis, gonorrhoea, granuloma inguinale, Haverhill fever, infected burns, infections in the oral region, infections associated with prostheses, intraabdominal abscesses, Legionnaire's disease, leprosy, leptospirosis, listeriosis, liver abscesses, Lyme disease, lymphogranuloma venerium, mastitis, mastoiditis, meningitis and infections of the nervous system, mycetoma, nocardiosis, non-specific urethritis, opthalmia, osteomyelitis, otitis, orchitis, pancreatitis, paronychia, pelveoperitonitis, peritonitis, peritonitis with appendicitis, pharyngitis, phlegmons, pinta, plague, pleural effusion, pneumonia, postoperative wound infections, postoperative gas gangrene, prostatitis, pseudo-membranous colitis, psittacosis, pulmonary emphysema, pyelonephritis, pyoderma, Q fever, rat-bite fever, reticulosis, ricin poisoning, Ritter's disease, salmonellosis, salpingitis, septic arthritis, septic infections, septicameia, sinusitis, skin infections, syphilis, systemic infections, tonsillitis, toxic shock syndrome, trachoma, tularaemia, typhoid, typhus, urethritis, wound infections, yaws, aspergillosis, candidiasis, cryptococcosis, favus, histoplasmosis, intertrigo, mucormycosis, tinea, onychomycosis, pityriasis versicolor, ringworm and sporotrichosis.

15. A pharmaceutical composition comprising 4-methyl-8-phenoxy-1-(2-phenylethyl)-2,3-dihydro-1H-pyrrolo[3,2-c]quinoline, an aminoglycoside antimicrobial agent, and a pharmaceutically acceptable adjuvant, diluent or carrier.

16. A pharmaceutical composition according to claim 15 which is formulated for oral or topical administration.

17. A pharmaceutical composition according to claim 15 which is formulated for administration by inhalation.

18. A method of treating a *Staphylococci, Streptococci, Pseudomonas, Bacillaceae, Enterobacteriaceae, Haemophilis influenzae, Enterococci, Mycobacteria, Aspergillus fumigatus, Candida albicans, Cryptococcus neoformans, Histoplasma capsulatum* or *Pneumocystis jiroveci* infection comprising simultaneously, separately or sequentially administering a combination comprising 4-methyl-8-phenoxy-1-(2-phenylethyl)-2,3-dihydro-1H-pyrrolo[3,2-c]quinoline and an aminoglycoside antimicrobial agent.

19. The method of claim 18 comprising killing multiplying microorganisms associated with a microbial infection.

20. The method of claim 18 comprising killing non-multiplying microorganisms associated with a microbial infection.

21. The method of claim 18 comprising killing clinically latent microorganisms associated with a microbial infection.

22. The combination of claim 1, wherein the aminoglycoside antimicrobial agent is 0.01-10 weight percent of the combination.

23. The pharmaceutical composition of claim 15, wherein the aminoglycoside antimicrobial agent is 0.01-10 weight percent of the pharmaceutical composition.

24. The method of claim 18, wherein the aminoglycoside antimicrobial agent is 0.01-10 weight percent of the combination.

* * * * *